(12) United States Patent
Keating et al.

(10) Patent No.: US 7,717,936 B2
(45) Date of Patent: May 18, 2010

(54) DEVICE FOR LOADING AN EMBOLIC PROTECTION FILTER INTO A CATHETER

(75) Inventors: Ronan Keating, Knocknacarra (IE); David Vale, Contarf (IE); John Neilan, Gort (IE)

(73) Assignee: Salviac Limited, Dublin (IE)

( * ) Notice: Subject to any disclaimer, the term of this patent is extended or adjusted under 35 U.S.C. 154(b) by 893 days.

(21) Appl. No.: 11/408,732

(22) Filed: Apr. 18, 2006

(65) Prior Publication Data

US 2007/0005102 A1 Jan. 4, 2007

Related U.S. Application Data

(60) Provisional application No. 60/672,442, filed on Apr. 18, 2005.

(51) Int. Cl.
*A61M 29/00* (2006.01)
(52) U.S. Cl. .................................................. 606/200
(58) Field of Classification Search ............... 606/113, 606/114, 127, 159, 191–198, 200; 623/1.11–1.2
See application file for complete search history.

(56) References Cited

U.S. PATENT DOCUMENTS

| | | | |
|---|---|---|---|
| 6,187,016 B1 * | 2/2001 | Hedges et al. | 606/108 |
| 2002/0049467 A1 * | 4/2002 | Gilson et al. | 606/200 |

\* cited by examiner

*Primary Examiner*—Kevin T Truong
(74) *Attorney, Agent, or Firm*—Sughrue Mion, PLLC

(57) ABSTRACT

A transvascular embolic protection system for safely capturing and retaining embolic material released during an interventional procedure comprises an embolic protection device (1) and a delivery catheter (2) for delivery of the embolic protection device (1) to a desired location in the vascular system. A pack (4) is provided to safely store and prepare the embolic protection system for use. The pack (4) comprises a tray (5) with a channel (6) extending in a looped configuration around the tray (5) for receiving the delivery catheter (2). A loading device (7) is mounted in the tray (5) adjacent to the delivery catheter (2). The embolic protection device (1) is mounted in an expanded configuration in a well (90) in the tray (5). A pushing device (8) for loading the collapsible embolic protection device (1) into the delivery catheter (2) is mounted in the tray (5) adjacent to the embolic protection device (1).

13 Claims, 35 Drawing Sheets

SECTION A-A

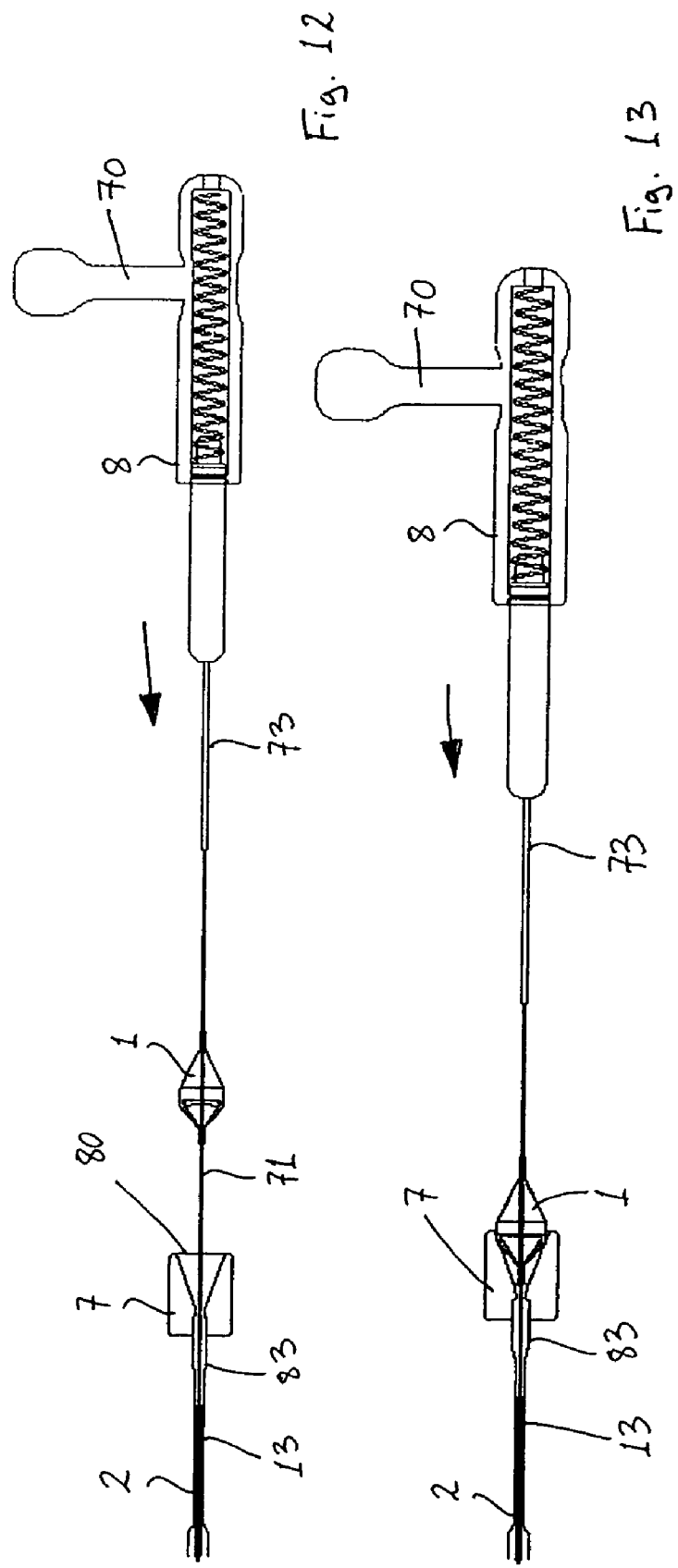

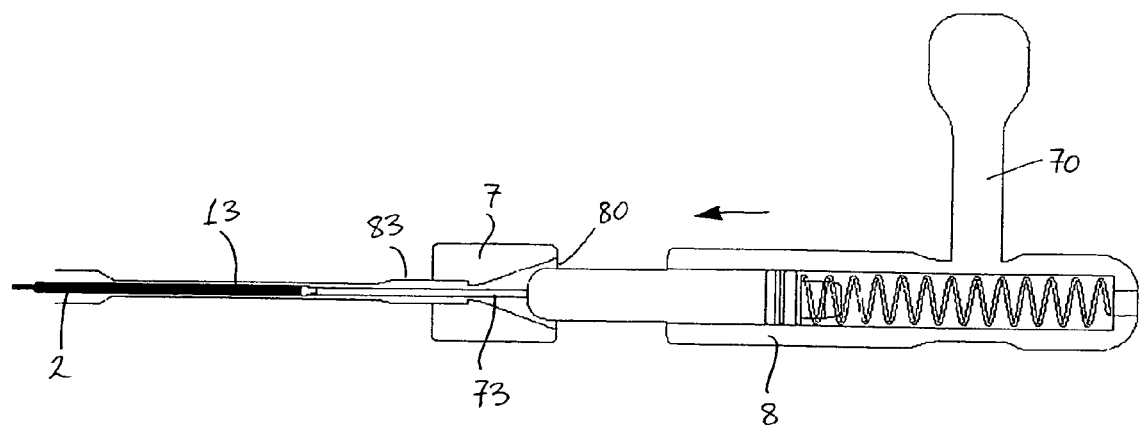
Fig. 14
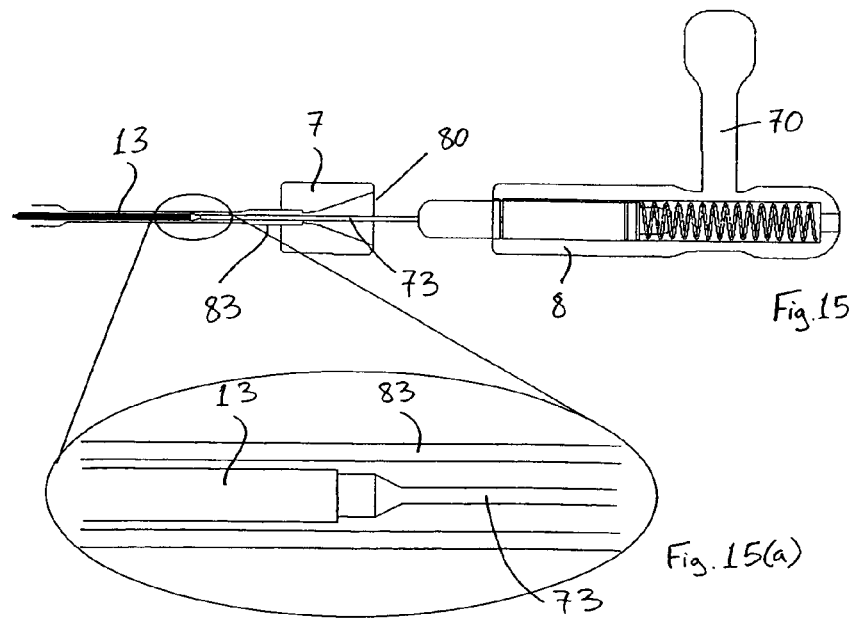
Fig. 15
Fig. 15(a)

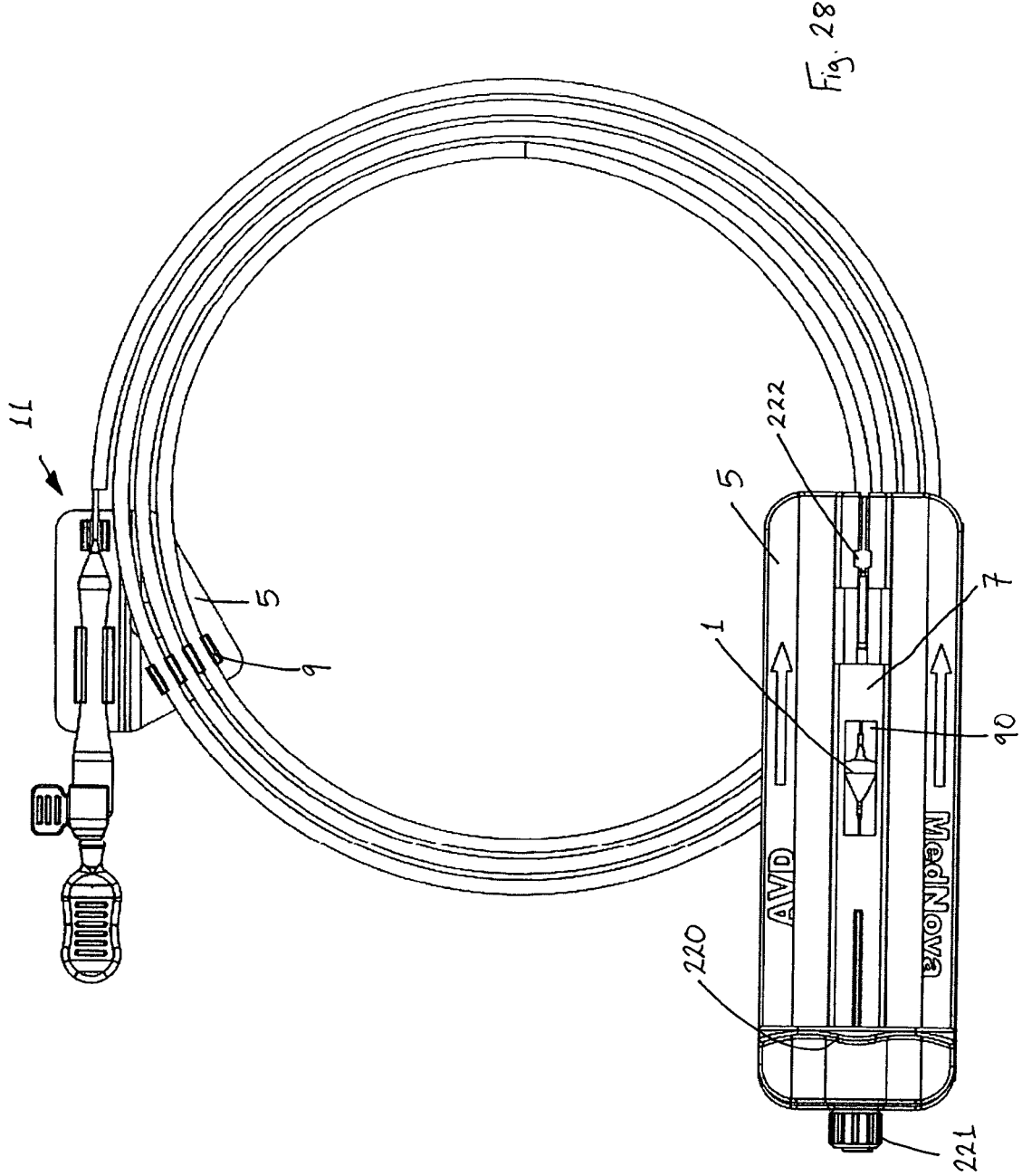

DEVICE FOR LOADING AN EMBOLIC PROTECTION FILTER INTO A CATHETER

RELATED APPLICATION

This application claims the benefit of U.S. patent application Ser. No. 60/672,442, filed Apr. 18, 2005, the entire teachings of which are incorporated herein by reference.

INTRODUCTION

This invention relates to a device and a method for loading an embolic protection filter into a catheter.

STATEMENTS OF INVENTION

According to the invention there is provided a device for loading an embolic protection filter into a catheter, the device comprising:
- an engagement member for engaging an embolic protection filter to load the embolic protection filter into a catheter; and
- a controller to control the loading force exerted on the embolic protection filter during loading into the catheter.

By controlling the loading force exerted, the controller prevents damage being inadvertently caused during loading of the filter.

The controller prevents the user inadvertently applying an excessive loading force to the embolic protection filter, for example when the filter is fully loaded into the catheter. If this were to occur, this extra loading force could lead to damage to the filter and/or to the catheter, and/or could lead to the loaded filter being incorrectly positioned in the catheter.

In one embodiment of the invention the controller is provided by a first part of the device being movable relative to a second part of the device. The first part of the device may be movable relative to the second part of the device between an extended configuration and a retracted configuration. The device may be biased towards the extended configuration. The device may comprise a biasing member to bias the device towards the extended configuration. The biasing member may comprise a coiled spring.

In another embodiment the first part of the device comprises a handle part. The second part of the device may comprise the engagement member.

In a further embodiment the engagement member comprises a pusher for engaging an embolic protection filter to push the embolic protection filter into a catheter. The engagement member may comprise a puller for engaging an embolic protection filter to pull the embolic protection filter into a catheter.

The engagement member may be provided on an elongate stem. The engagement member may be integral with the stem. The engagement member may comprise a step in the stem from a small diameter portion to a large diameter portion. The stem may comprise a wire.

In another aspect the invention provides a method of loading an embolic protection filter into a catheter, the method comprising the steps of:
- engaging the embolic protection filter; and
- loading the embolic protection filter into the catheter, the loading force exerted on the embolic protection filter being automatically controlled during loading.

In one embodiment loading of the embolic protection filter into the catheter causes a first part of a controller to move relative to a second part of the controller. The embolic protection filter may be loaded into the catheter by pushing the embolic protection filter into the catheter. The embolic protection filter may be loaded into the catheter by pulling the embolic protection filter into the catheter.

In another aspect of the invention, there is provided a device for loading an embolic protection filter into a catheter, the device comprising:
- a loading member for collapsing an embolic protection filter;
- an outlet of the loading member, being configured to be aligned with an inlet of a catheter extending along at least part of an exterior surface of the catheter for loading of the collapsed embolic protection filter into the catheter.

Because the outlet of the loading member extends along the exterior surface of the catheter, this ensures that, when the embolic protection filter is loaded, the loaded catheter can be quickly and simply disassociated from the loading member, and inserted into the vasculature of a patient. In particular the loaded catheter may be quickly withdrawn from the catheter without the risk that the embolic protection filter will remain in the loading member. In addition during loading of the embolic protection filter, it is not necessary to move the catheter relative to the loading member to effect a complete loading of the filter into the catheter.

Furthermore the wall space and profile of the catheter assembly may be minimised by arranging the outlet of the loading member along the exterior of the catheter.

In one embodiment the loading member has a passageway extending therethrough, through which an embolic protection filter may be passed to collapse the embolic protection filter. The outlet of the loading member may comprise an outlet of the passageway. An inlet of the passageway may have a larger cross-sectional area than the outlet of the passageway. The passageway may be at least partially funnel-shaped.

In another embodiment the loading member comprises a tubular part extendable along part of an exterior surface of a catheter, the outlet of the loading member being provided at an end of the tubular part. The passageway may extend through the tubular part in a substantially cylindrical shape.

In another embodiment the embolic protection system includes loading means for loading the filter into the delivery catheter. Ideally the loading means comprises a funnel having a narrowed portion disposed at the distal end of the delivery catheter and an enlarged portion for receiving a proximal portion of the filter in the expanded configuration, the filter being progressively collapsed as it is moved through the funnel for loading into the delivery catheter.

The invention also provides in another aspect a method of loading an embolic protection filter into a catheter, the method comprising the steps of:
- arranging a loading member relative to the catheter with an outlet of the loading member aligned with an inlet of the catheter and with the outlet of the loading member extending along at least part of an exterior surface of the catheter;
- collapsing the embolic protection filter; and
- loading the collapsed embolic protection filter into the catheter.

In another embodiment the embolic protection filter is collapsed by passing the embolic protection filter through the loading member. The method may comprise the step of disassociating the catheter from the loading member after loading of the collapsed embolic protection filter into the catheter. The catheter may be disassociated from the loading member by withdrawing the catheter from within the outlet of the loading member. The catheter may be withdrawn by gripping the catheter and moving the catheter while the loading member remains stationary.

In another aspect of the invention there is provided an assembly for loading an embolic protection filter into a catheter, the assembly comprising one or more devices of the invention.

In a further aspect the invention provides a device for loading an embolic protection filter into a catheter, the device comprising:

an engagement member for engaging an embolic protection filter to move the embolic protection filter relative to a catheter to load the embolic protection filter into the catheter;

the loading device being configured to automatically flush the embolic protection filter and/or the catheter upon movement of the engagement member relative to the catheter.

By automatically flushing the embolic protection filter and the catheter during the loading of the filter into the catheter, this provides for a faster and simpler preparation, before the loaded catheter is inserted into the vasculature of a patient.

In one embodiment the device comprises a bath for immersing an embolic protection filter in a flushing liquid before loading into a catheter. The bath may be sealable. Because the bath can be sealed, the filter can be stored and/or transported while immersed in the flushing liquid for potentially relatively long periods of time. The engagement member may be movable relative to the bath to move an embolic protection filter relative to a catheter. The engagement member may be configured to move relative to the bath while maintaining a seal with a wall of the bath. The engagement member may comprise a plunger.

In another embodiment the device comprises a lock to lock the position of the engagement member. The device may comprise a stop to resist movement of the catheter during loading of the embolic protection filter. The stop may be configured to facilitate movement of the catheter after loading.

In a further embodiment the engagement member comprises a pusher for engaging an embolic protection filter to push the embolic protection filter into a catheter. The engagement member may comprise a puller for engaging an embolic protection filter to pull the embolic protection filter into a catheter. The device may comprise a controller to control the loading force exerted on the embolic protection device during loading into a catheter. The controller may comprise a coiled spring.

The invention provides in a further aspect a method of loading an embolic protection filter into a catheter, the method comprising the steps of:

engaging the embolic protection filter;

moving the embolic protection filter relative to the catheter to load the embolic protection filter into the catheter;

the step of moving the embolic protection filter relative to the catheter causing an automatic flushing of the embolic protection filter and/or the catheter.

In one embodiment the embolic protection filter is immersed in a flushing liquid before loading. The method may comprise the step of sealing the embolic protection filter immersed in the flushing liquid. The step of moving the embolic protection filter relative to the catheter may cause at least some of the flushing liquid to move relative to the embolic protection filter and/or relative to the catheter. The embolic protection filter may be pushed into the catheter. The embolic protection filter may be pulled into the catheter.

BRIEF DESCRIPTION OF THE DRAWINGS

The invention will be more clearly understood from the following description of some embodiments thereof, given by way of example only, with reference to the accompanying drawings, in which:

FIGS. 12 to 15 are side views illustrating loading of the embolic protection filter of FIG. 1 into the catheter assembly using the first loading device of FIGS. 2 to 4 and the second loading device of FIG. 6;

FIG. 15(a) is an enlarged, side view of the embolic protection filter loaded into the catheter assembly;

FIGS. 28 and 29 are perspective views of a further pack containing an embolic protection filter, a catheter assembly, and a device according to the invention for loading the embolic protection filter into the catheter assembly;

DETAILED DESCRIPTION

Figure 1:
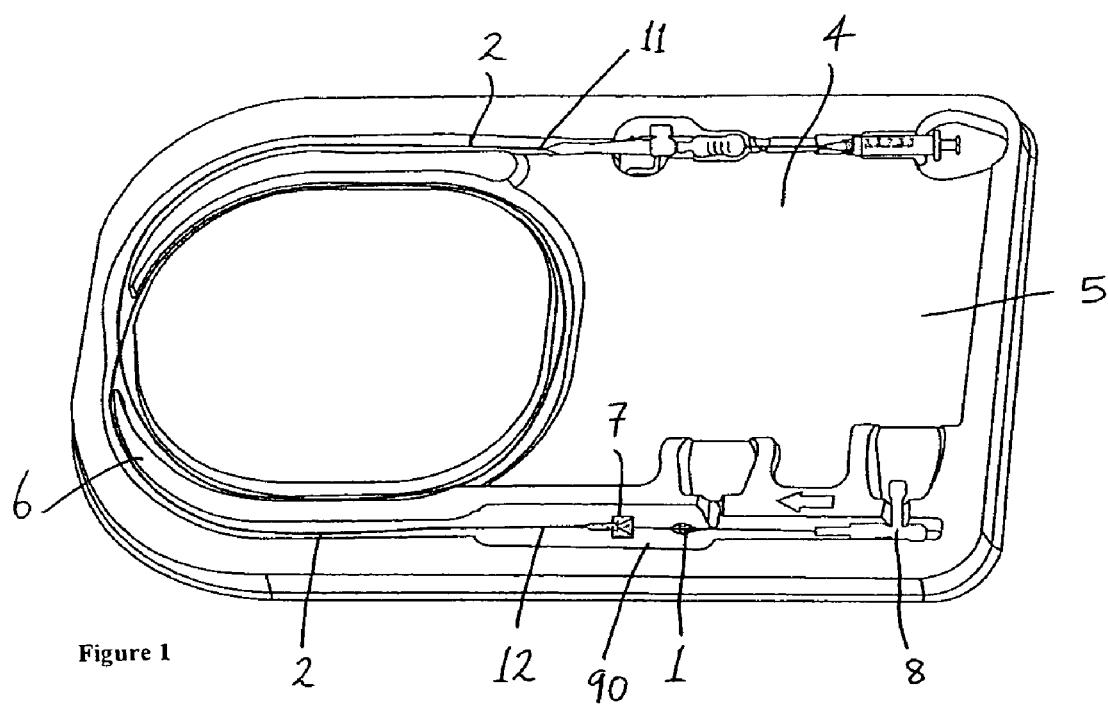
FIG. 1 is a perspective view of a pack containing an embolic protection filter, a catheter assembly, and two devices according to the invention for loading the embolic protection filter into the catheter assembly.

Referring to the drawings, and initially to FIGS. 1 to 17 thereof, there is illustrated a transvascular embolic protection system for safely capturing and retaining embolic material released during an interventional procedure while maintaining blood flow.

The embolic protection system comprises an embolic protection device 1 and a delivery catheter 2 for delivery of the embolic protection device 1 to a desired location in the vascular system. The device 1 is collapsible from an expanded deployed configuration to a retracted delivery configuration. The delivery catheter 2 has a pod 13 at the distal end to define a reception space for the embolic protection device 1 in the collapsed delivery configuration.

In use, the embolic protection device 1 is loaded into the pod 13 of the delivery catheter 2 which is delivered over a pre-positioned guidewire. At a desired location, the embolic protection device 1 is deployed from within the pod 13. The delivery catheter 2 is then withdrawn leaving a bare guidewire over which various devices such as a dilation balloon and/or a stent can be advanced to the treatment site. Embolic material dislodged during the treatment procedure(s) is collected in the embolic protection device 1. After treatment, the device 1 may be retrieved into a retrieval catheter. The guidewire may be left in place for further catheter advancements or may be withdrawn with or subsequent to the withdrawal of the retrieval catheter.

Referring in particular to FIG. 1, a pack 4 is provided to safely store and prepare the embolic protection system for use. The pack 4 comprises a vacuum-formed tray 5, typically of PETG. The tray 5 has a channel 6 extending in a looped configuration around the tray 5 for receiving the delivery catheter 2. The delivery catheter 2 has a distal end 12. The pod 13 is provided at the distal end 12 of the inner catheter 2. A loading device 7 according to the invention, which in this case is in the form of a funnel piece, is mounted in the tray 5 adjacent to and extending along an exterior surface of the pod 13. The embolic protection device 1 is mounted in its expanded configuration in a well 90 in the tray 5. A pushing device 8 according to the invention for loading the collapsible embolic protection device 1 into the delivery catheter 2 is mounted in the tray 5 adjacent to the embolic protection device 1. The pushing device 8 is used to push the embolic protection device 1 through the loading device 7 and into the pod 13 of the delivery catheter 2 in the collapsed configuration. The delivery catheter 2 is now ready for advancement over a guidewire.

Referring now to FIGS. 2 to 5, the pushing device 8 according to the invention for loading the collapsible filter element into the pod 13 of the delivery catheter 2 is illustrated. The pushing device 8 comprises a handle 70 for gripping the pushing device 8 and an elongate stem in this case provided by a wire 71, extending from the handle 70 for threading through the filter element. The wire 71 defines an engagement member, in this case provided in the form of a distal stop 72, for releasably engaging with the distal end of a sleeve of a filter element to push the filter element into the pod 13 of the delivery catheter 2.

Figure 5:
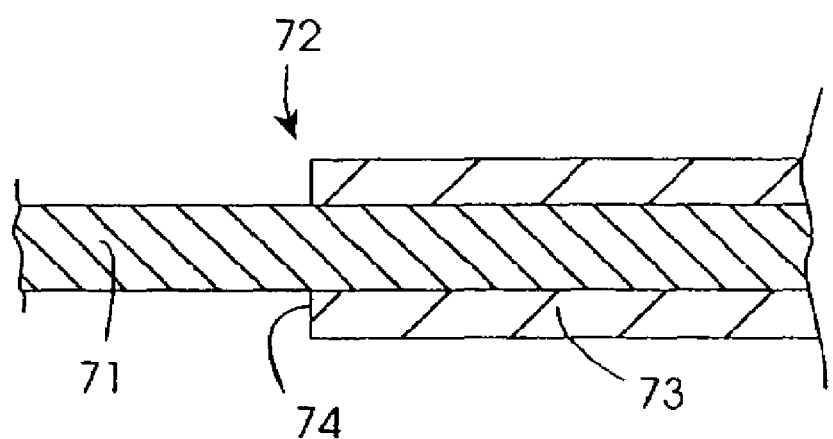
FIG. 5 is an enlarged, cross-sectional, side view of a part of the first loading device of FIGS. 2 to 4.

As illustrated in FIG. 5 the distal stop 72 is provided by an end 74 of an outer hypotube 73 which extends from the handle 70 partially along the wire 71. The free end 74 of the hypotube 73 forms a step from the small diameter wire 71 proximal of the step to the larger diameter hypotube 73 distal of the step. The small diameter is preferably approximately 0.014" (0.3556 mm), and the large diameter is preferably approximately 0.018" (0.4572 mm). The hypotube 73 may be attached to the wire 71 by any suitable means, such as an adhesive means, or a mechanical keying means, or by brazing, or soldering, or welding, or by any other suitable means.

Figure 2:
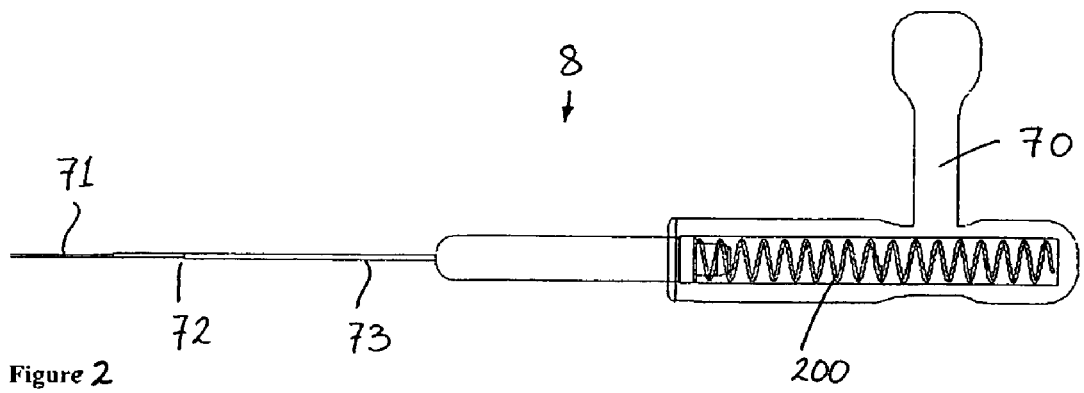
FIGS. 2 to 4 are cross-sectional, side views of the first loading device of FIG. 1.
Figure 3:
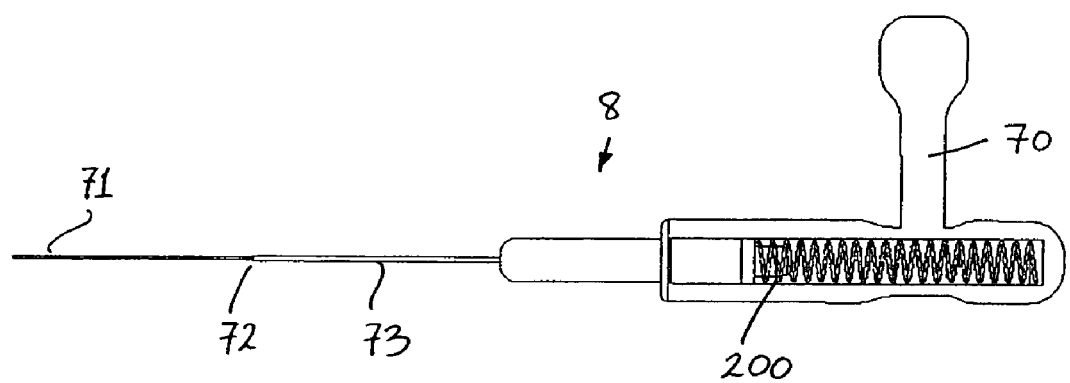
Figure 4:
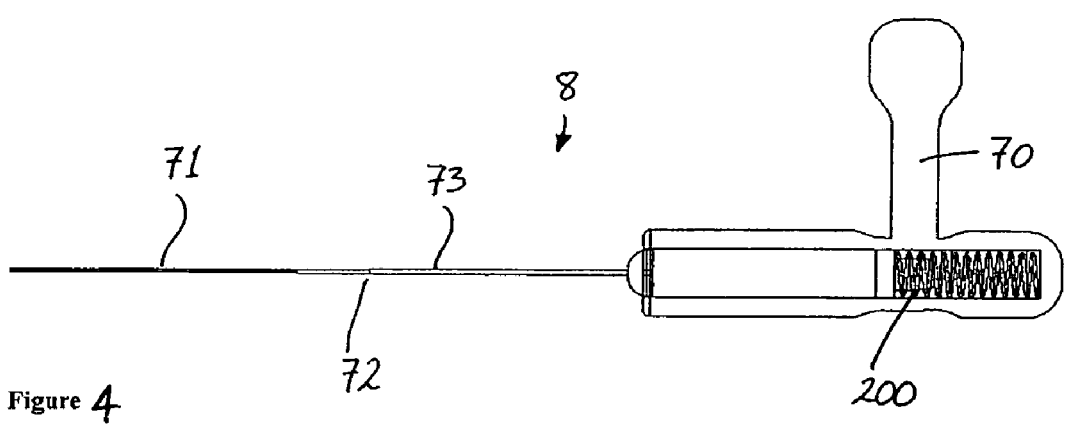

As illustrated in FIGS. 2 to 4, the handle 70 is movable relative to the wire 71 between an extended configuration (FIG. 2) and a retracted configuration (FIG. 4). A coiled spring 200 is housed within the handle 70 bearing against the wire 71 to bias the pushing device 8 towards the extended configuration.

Upon engagement of the distal stop 72 with the filter element and pushing of the filter element, the engagement pushing force applied by the wire 71 on the filter element is balanced by an equal and opposite force exerted by the filter element on the wire 71. As the pushing force is increased to load the filter element, the opposite force gradually overcomes the biasing force of the spring 200, causing the spring 200 to compress and thereby moving the pushing device 8 from the extended configuration (FIG. 2) to the retracted configuration (FIG. 4).

The stiffness of the spring 200 is selected to enable a safe loading force to be applied to load the filter element into the pod 13 of the delivery catheter 2. However if it is attempted to apply an excessive loading force the spring 200 compresses, thus preventing excessive loads being transferred to the system. Thus the movement of the handle 70 relative to the wire 71 acts as a controller to control the loading force exerted on the filter element during loading into the delivery catheter 2. In this way, the device 8 allows a safe loading force to be applied to the system, and prevents damage being inadvertently caused due to excessive loading forces.

The wire 71 may have a low friction coating, for example of polytetrafluoroethylene, for ease of threading of the wire 71 through the filter element. The handle 70 facilitates ease of gripping and of use of the pushing device 8.

It will be appreciated that the distal stop 72 may be provided integral with the wire 71, for example by machining a step in the wire 71.

It will further be appreciated that the large diameter portion distal of the step may be only a locally defined feature on the wire 71 that does not extend distally to the handle 70.

It will be appreciated that the filter element may alternatively be pulled into the pod 13 of the delivery catheter 2 using a suitable pulling device.

Figure 6:
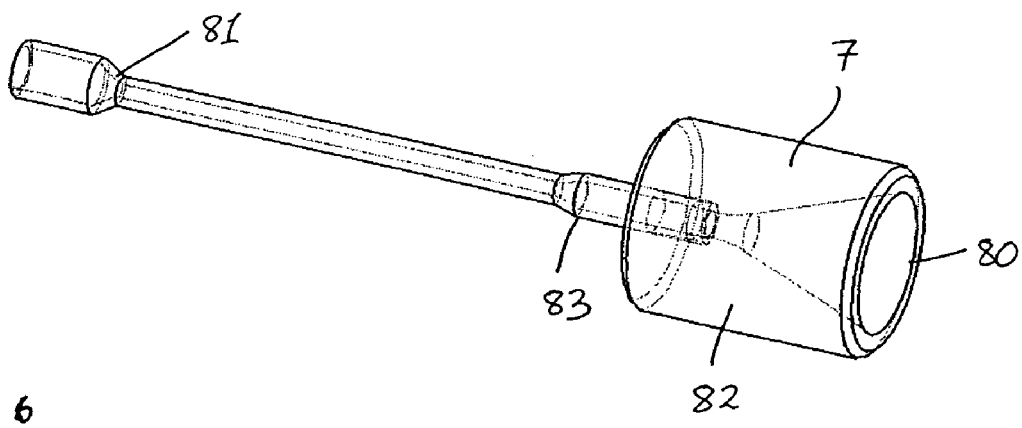
FIG. 6 is a perspective view of the second loading device of FIG. 1.
Figure 7:
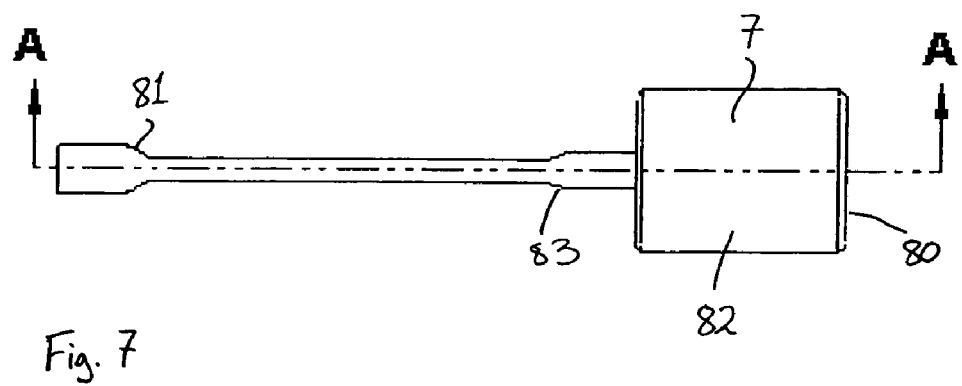
FIG. 7 is a side view of the second loading device of FIG. 6.
Figure 8:
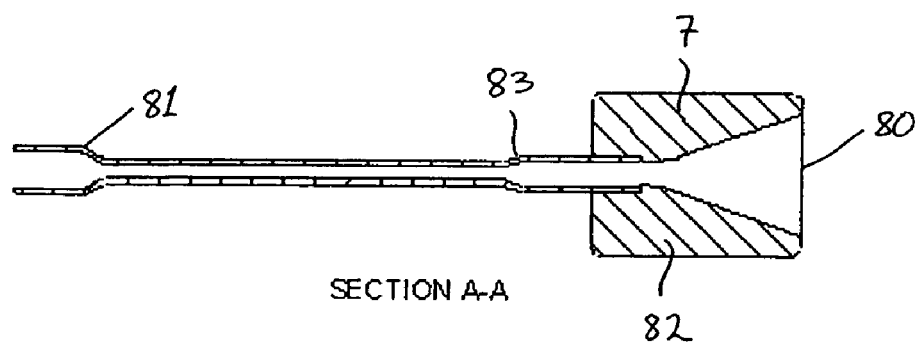
FIG. 8 is a cross-sectional, side view of the second loading device of FIG. 6.

The loading device 7 for loading the filter element into the pod 13 of the delivery catheter 2 is illustrated in detail in FIGS. 6 to 8. The loading device 7 defines a funnel having an inlet end 80 and an outlet end 81, the inlet end 80 defining a larger cross-sectional area than the outlet end 81, and the outlet end 81 being configured for co-operative alignment with the inlet of the delivery catheter 2, and for extending along the exterior surface of the delivery catheter 2.

The loading device 7 has means for collapsing the filter element by radially compressing the filter element from the extended outwardly projecting position to the collapsed position. In this case, the loading device 7 comprises a main support 82 having a funnel-shaped bore formed from a frusto-conical filter element receiving portion terminating and a cylindrical portion formed by a thin walled loading tube 83 projecting from the main support 82 for positioning extending along the exterior surface of the delivery catheter 2. A passageway is provided through the main support 82 and through the loading tube 83. By passing the filter element through the passageway, the filter element is collapsed.

The cone angle of the bore is chosen from an angle in the range of between 15° and 65°, preferably between 35° and 45°.

The loading tube 83 is preferably formed from polyethyleneterephthalate (PET), and is mounted on a metal spigot, typically a grit blasted hypotube, by a combination of a polyolefin shrink tube bond and an adhesive bond. The metal spigot is adhesively fixed to the main support 82 which is formed from "Perspex" or a similar material. The loading tube 83 may be coated with a lubricant.

Referring to FIGS. 1 and 9 to 11, the tray 5 will now be described in further detail. The tray 5 includes integral projections 9 that extend into various recesses. The projections 9 releasably support the loading device 7 in co-operative alignment with the delivery catheter 2 before loading and during the loading procedure. In particular, the loading device 7 is supported with the loading tube 83 extending proximally along an exterior surface of the delivery catheter 2 before loading and during the loading procedure. In addition, the projections 9 on the channel wall are configured to releasably support the pushing device 8 in a position in which the distal stop 72 does not engage the filter element before the loading procedure commences.

A liquid retaining bath 90 is provided by a recess in the tray 5, the bath 90 having a depth sufficient to accommodate in a totally submerged state the reception space of the delivery catheter 2 and the filter element for submerged loading of the filter element through the loading device 7 and into the pod 13 of the delivery catheter 2. As illustrated in FIG. 1, the channel 6 communicates with the bath 90.

The components of the embolic protection system are placed in the pack 4 in the following manner. The loading device 7 is snapped into place in the channel 6, with the projections 9 releasably supporting the loading device 7 in the position illustrated in FIG. 1.

The catheter 2 is looped through the channel 6 and held in place so that the loading tube 83 of the loading device 7 extends proximally along the exterior surface of the delivery catheter 2, and the outlet end 81 of the loading tube 83 is aligned with the inlet of the delivery catheter 2.

The wire 71 of the pushing device 8 is then threaded through the filter element, a proximal end of the wire 71 is inserted through the loading device 7 and extended partially through the catheter 2. The handle 70 is snapped into place in the channel 6 by the projections 9. In this configuration the filter element is slidable over the wire 71 but is normally positioned within the bath 90, as illustrated in FIG. 1. The projections 9 retain the pushing device 8 in a position in which the distal stop 72 is spaced distally of the bath 90, and so the distal stop 72 does not engage the filter element in this storage configuration, as illustrated in FIG. 1.

In this storage configuration the filter element is in the expanded configuration. The assembled pack 4 of the invention may be safely stored for long periods in a packaged configuration without risk of filter element material deformation, such as material creep. The pack 4 is placed in a porch and sealed.

When the assembled pack 4 is required for use, the seal is broken, and the pack 4 is removed.

Figure 9:
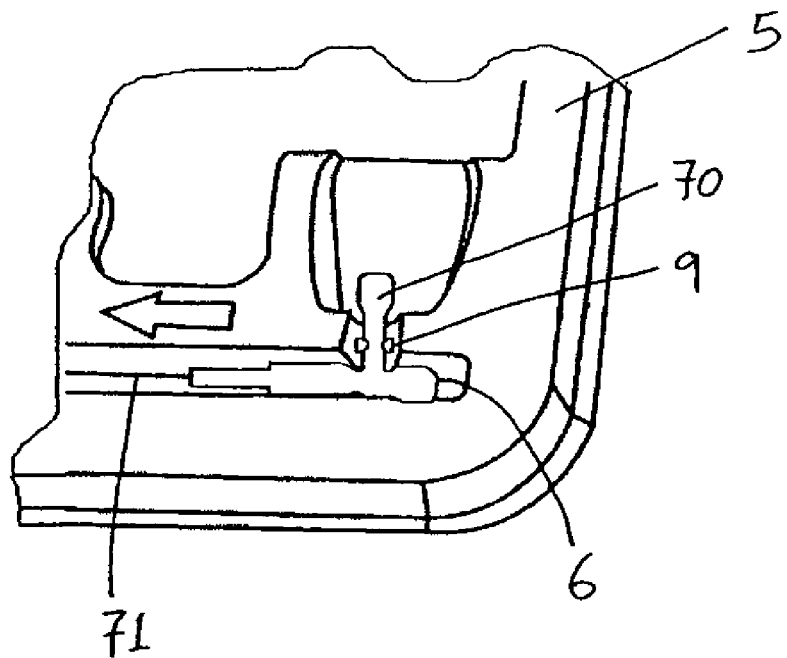
FIGS. 9 and 10 are perspective views illustrating release of the first loading device of FIG. 6.
Figure 10:
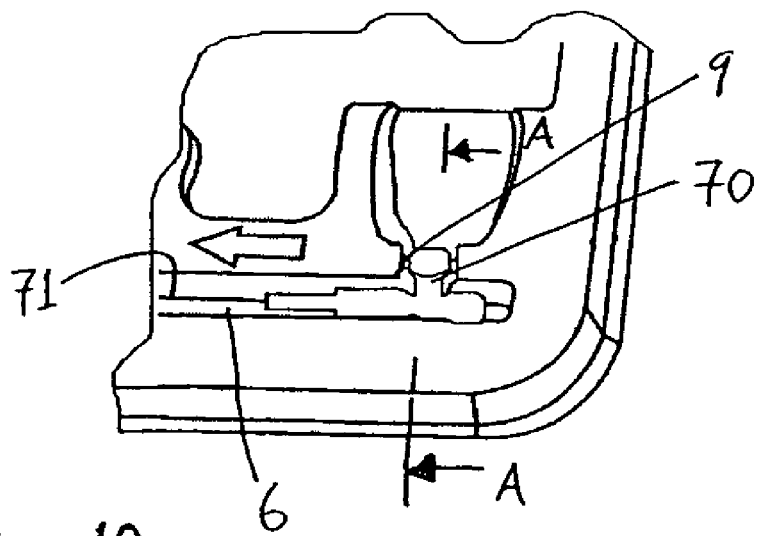
Figure 11:
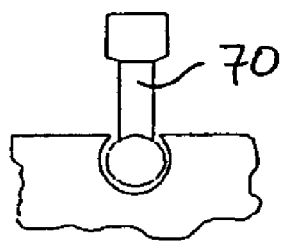
FIG. 11 is a view along line A-A in FIG. 10.

The filter element is now ready for loading into the pod 13 of the delivery catheter 2. The pushing device 8 is rotated through 90° in a "bolt-action" to release the handle 70 from the snap-fit retaining projections 9 in the tray 5, as illustrated in FIGS. 9 and 10. In this configuration the pushing device 8 is still retained in the tray 5 (FIG. 11). The pushing device 8 is now free to slide proximally in the channel 6, until the distal stop 72 engages with the distal end of the sleeve of the filter element (FIG. 12). Continued pushing of the pushing device 8 will push the filter element 40 proximally towards the loading device 7 (FIG. 13), through the loading device 7 (FIG. 14), thereby collapsing the filter element from the extended outwardly projecting position to the collapsed position, and loading the filter element into the pod 13 of the delivery catheter 2.

As the filter element is pushed through the loading device 7, the pushing force required to load the filter element gradually increases. This increase in force causes an initial compression of the spring 200, as illustrated in FIGS. 13 and 14. This initial compression is caused as a result of the loading of the filter into the pod 13.

The spring 200 then compresses further, as illustrated in FIGS. 14 and 15. This further compression accommodates any dimensional tolerances in the system. FIG. 15(*a*) illustrates the filter loaded into the pod 13, with the pod being located within the loading tube 83.

Figure 16:
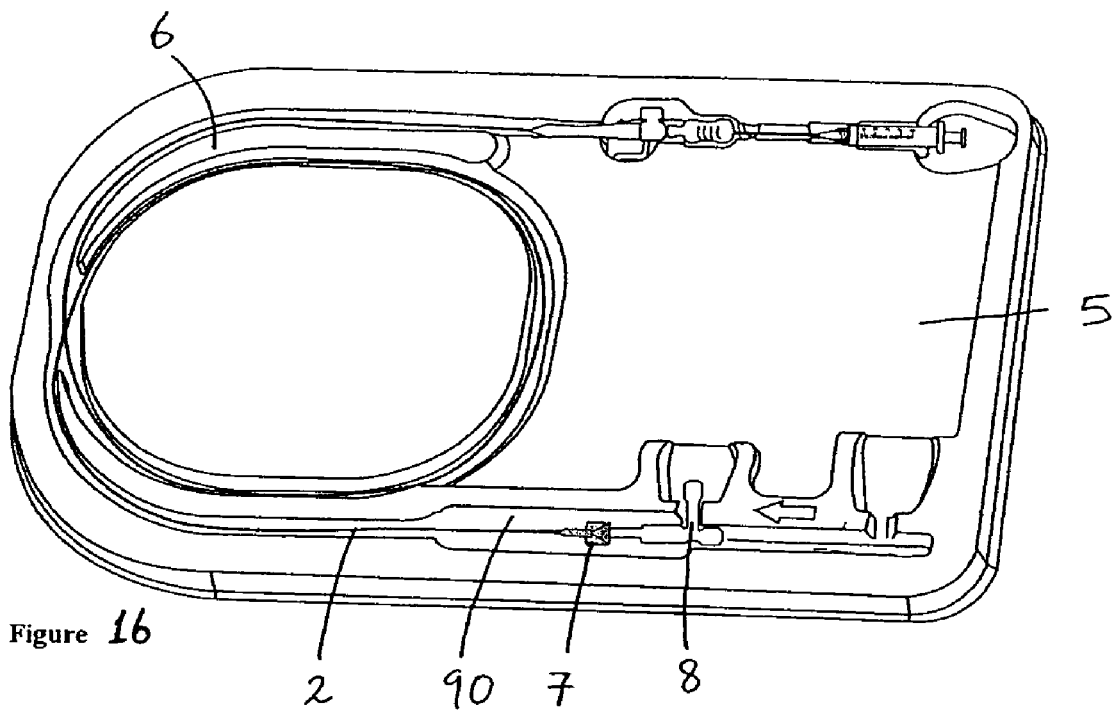
FIG. 16 is a perspective view of the pack of FIG. 1 after loading of the embolic protection filter of FIG. 1 into the catheter assembly.
Figure 17:
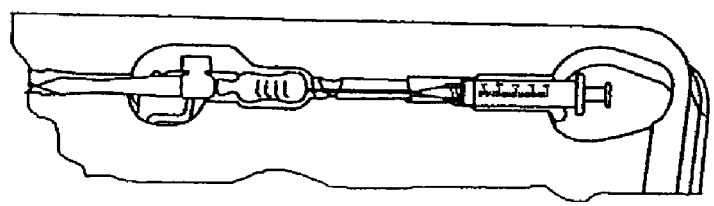
FIG. 17 is an enlarged, perspective view of a part of the pack of FIG. 16.
Figure 18:
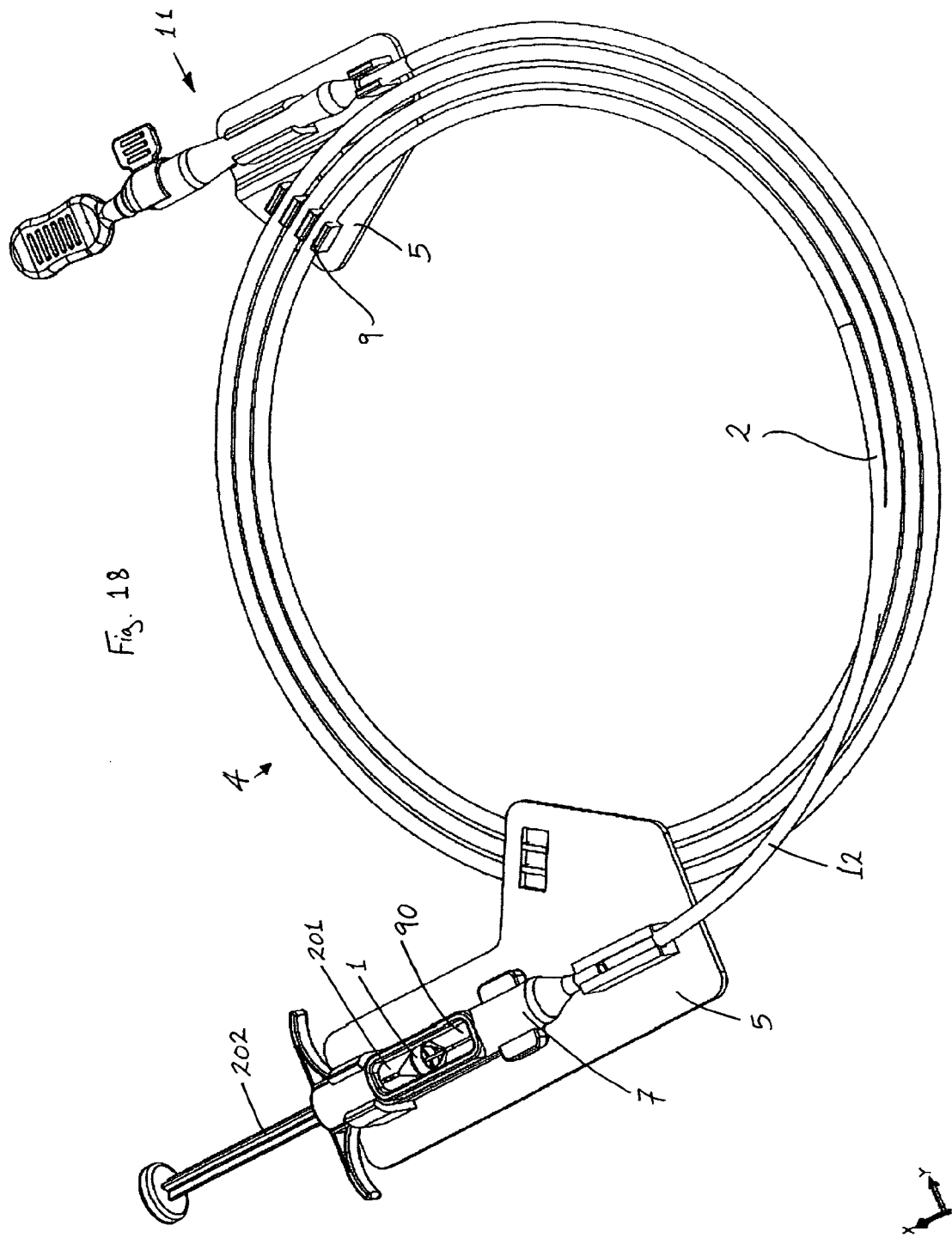
FIG. 18 is a perspective view of a pack containing an embolic protection filter, a catheter assembly, and a device according to the invention for loading the embolic protection filter into the catheter assembly.
Figure 19:
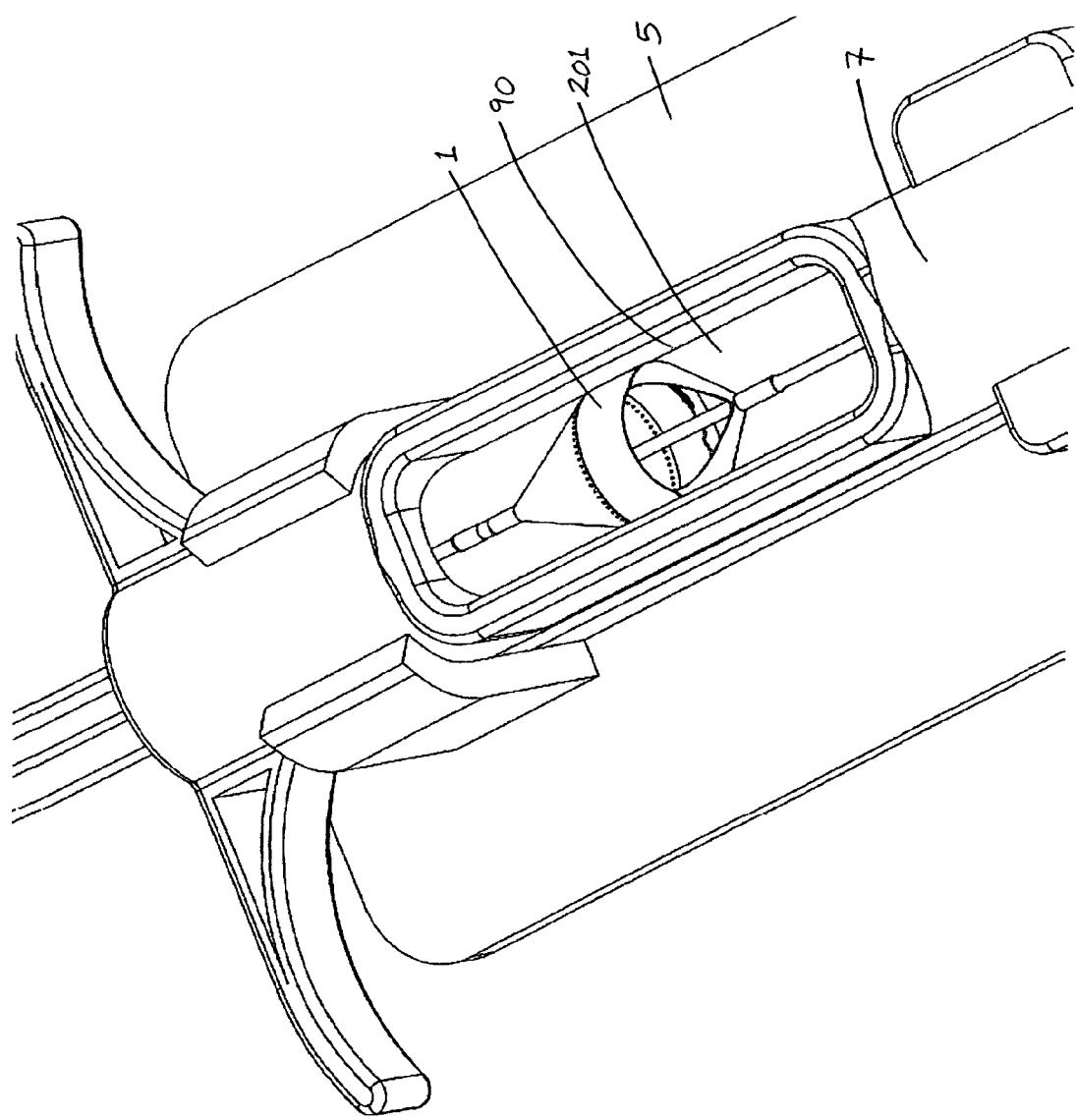
FIG. 19 is an enlarged, perspective view of the embolic protection filter and the loading device of FIG. 18.
Figure 20:
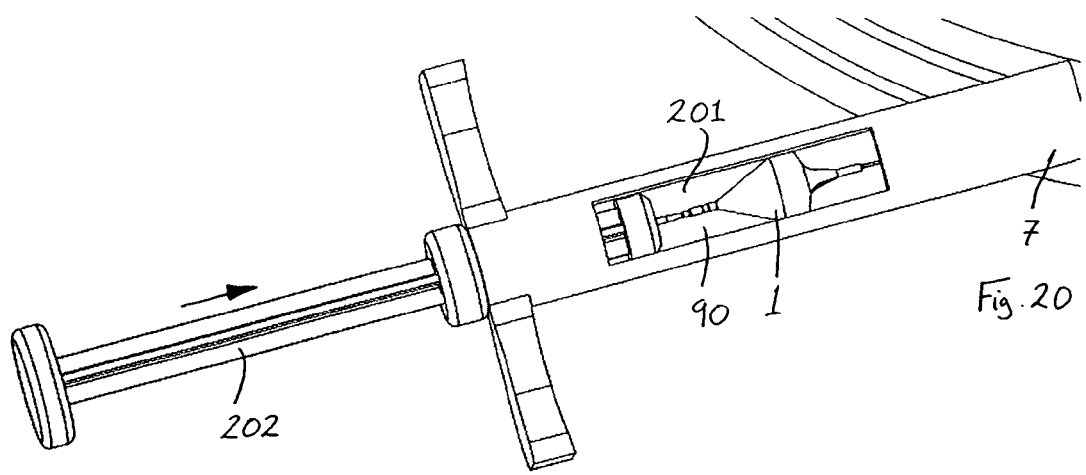
FIGS. 20 to 23 are perspective views illustrating loading of the embolic protection filter of FIG. 19 into the catheter assembly of FIG. 18.
Figure 21:
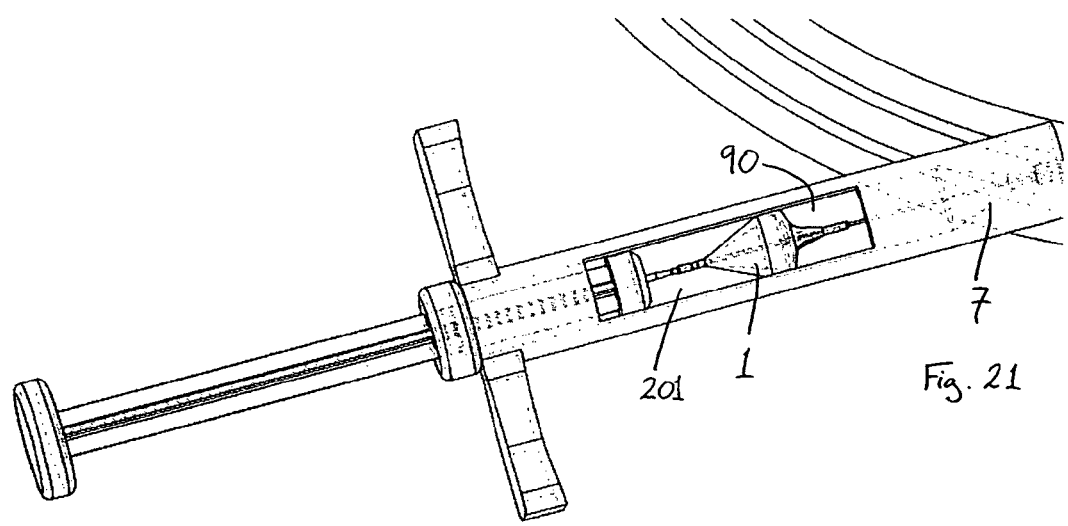
Figure 37:
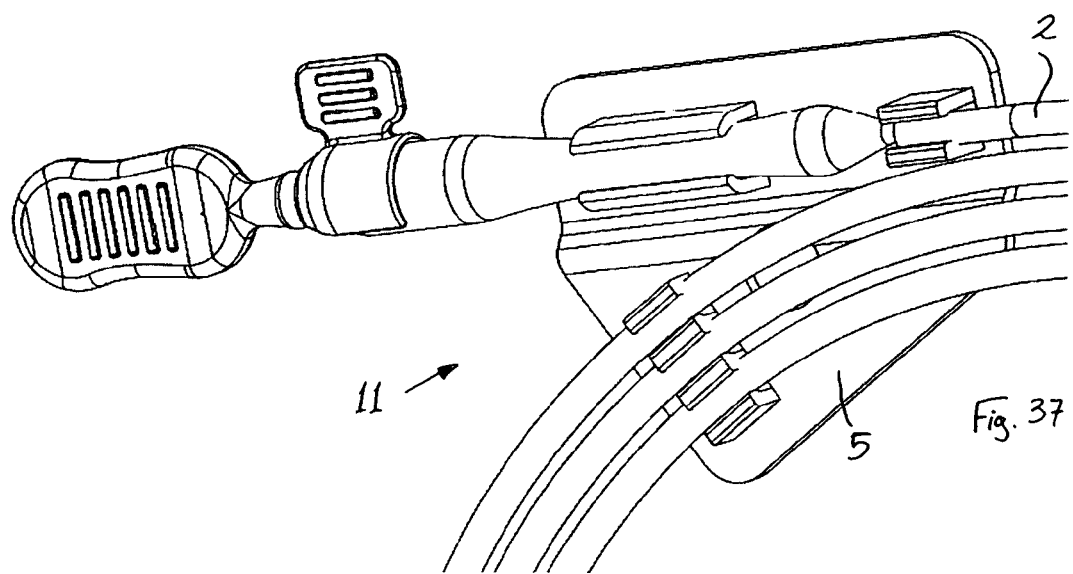
FIGS. 30 to 37 are enlarged, perspective views of parts of the pack of FIGS. 28 and 29.
Figure 22:
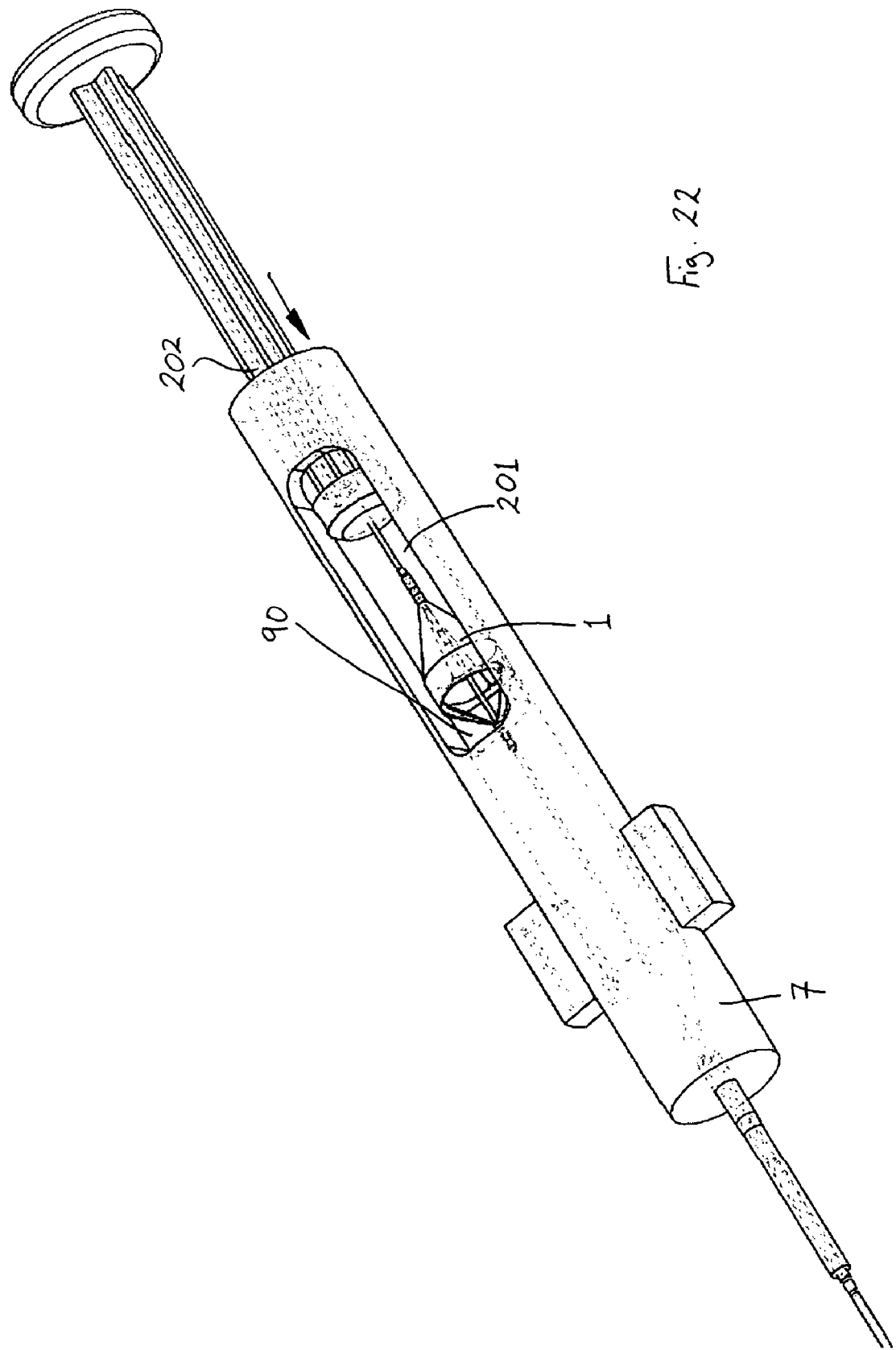

When the device 8 is in this retracted configuration with the spring 200 fully compressed, the handle 70 is snapped into position in a second recess by means of retaining projections 9 (FIG. 16). This second recess is spaced to ensure that the handle 70 may only be snapped into position when the spring 200 is fully compressed. This arrangement therefore guarantees that the correct loading force is applied and the filter is fully loaded.

The loading device 7 has thus far remained in co-operative alignment with the delivery catheter 2. The loaded catheter assembly may be gripped and pulled proximally in the channel 6 away from the stationary loading device 7 to withdraw the pod 13 of the delivery catheter 2 from within the outlet 81 of the loading tube 83. In this manner, the delivery catheter 2, and the collapsed filter element are moved together proximally away from the loading device 7, and thereby the loaded catheter assembly is disassociated from the loading device 7.

The loaded catheter assembly is then removed from the channel 6 leaving the loading device 7 and the pushing device 8 behind in the channel 6. The loaded delivery catheter 2 is now ready for insertion into a vascular system of a patient.

The components of the pack 4 are retained in the correct loading alignments by the tray 5. The pushing device 8 is completely separated from the loaded catheter assembly after completion of the loading procedure.

In addition, the loaded filter element is not attached or associated in any way with the pushing device 8. Thus, the user is free to choose any suitable guidewire, as desired, for subsequent delivery of the filter element through a vascular system of a patient.

Shortest catheter length: In one embodiment, when the filter is loaded, the spring has compressed by 20 mm, a 5 N load is placed on the filter.

Longest catheter length: In one embodiment, when the filter is loaded, the spring has compressed by 30 mm, a 6 N load is placed on the filter.

In FIGS. 18 to 23 there is illustrated another transvascular embolic protection system, which is similar to the system of FIGS. 1 to 17, and similar elements in FIGS. 18 to 23 are assigned the same reference numerals.

In this case the embolic protection device 1 is positioned in the bath 90, and the bath 90 is filled with a flushing liquid, such as a saline solution, to immerse the filter element. The bath 90 is then sealed with a transparent film 201. The assembled pack 4 may be stored with the saline solution sealed within the bath 90, until required for use.

Alternatively the bath 90 may be open and be filled with saline solution only when required for use.

The engagement member is provided in this case by a syringe plunger 202. The plunger 202 is movable through the bath 90 to engage the filter element, while maintaining a seal between the plunger 202 and the walls of the bath 90.

When the assembled pack 4 is required for use, the plunger 202 is depressed to push the filter element through the loading device 7 to collapse the filter element, and to load the filter element into the pod 13 of the delivery catheter 2.

Because the saline solution is sealed within the bath 90, the step of depressing the plunger 202 also causes the flushing liquid in the bath 90 to move around the filter element and through the catheter assembly, and thus automatically flush the filter element and the catheter assembly.

Figure 23:
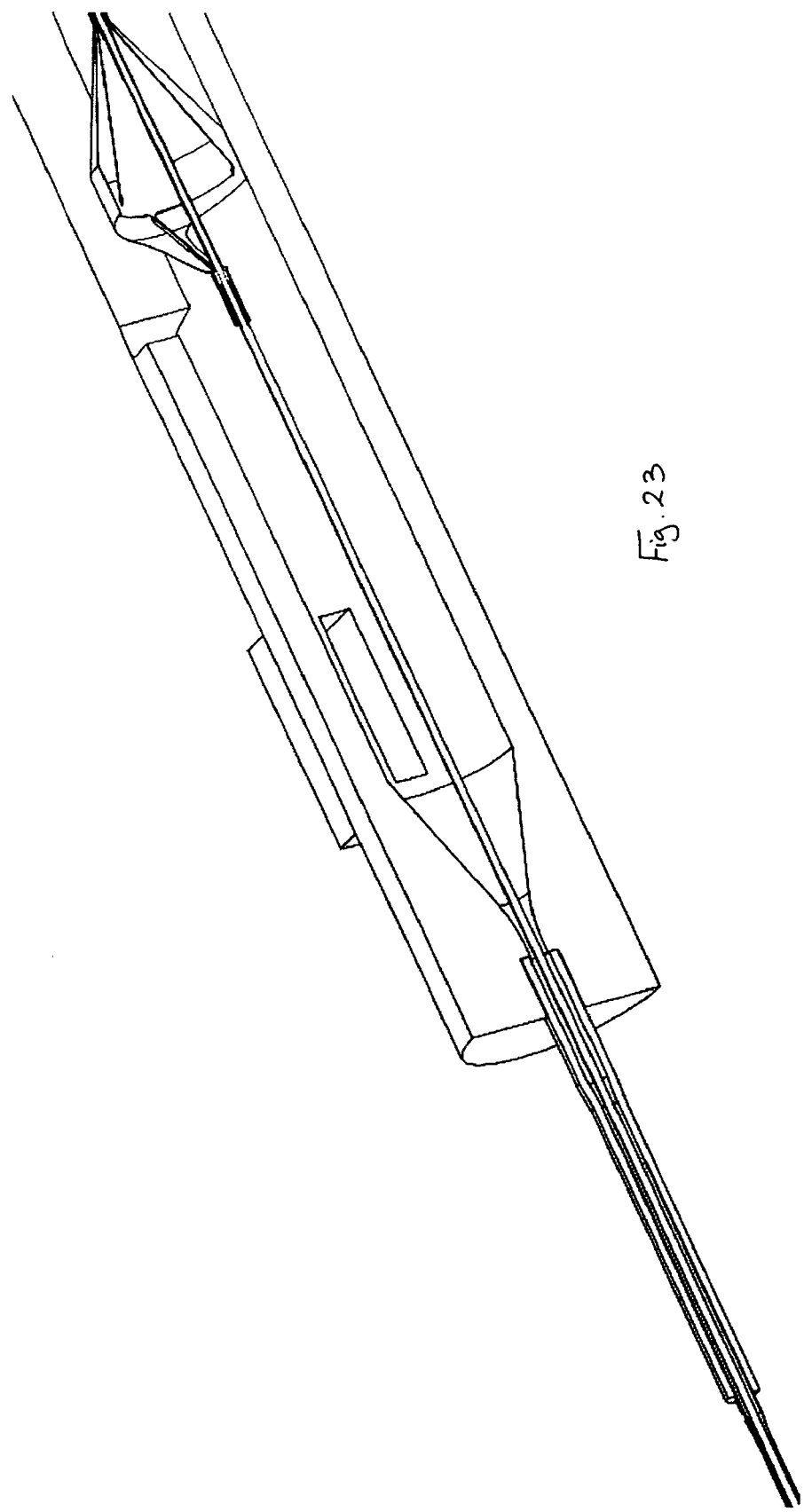
Figure 23A:
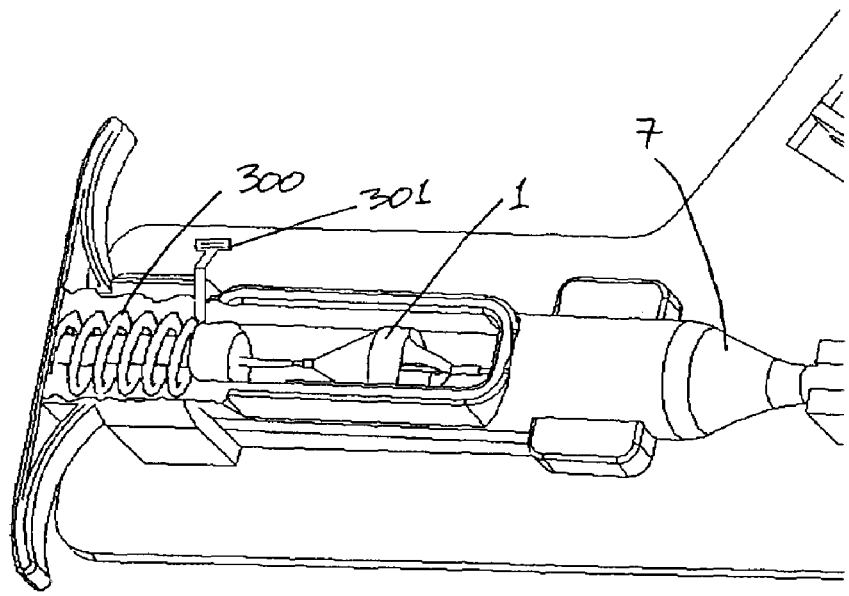
FIGS. 23(a) and 23(b) are partially cut-away, perspective views of another device according to the invention for loading an embolic protection filter into a catheter assembly.
Figure 23B:
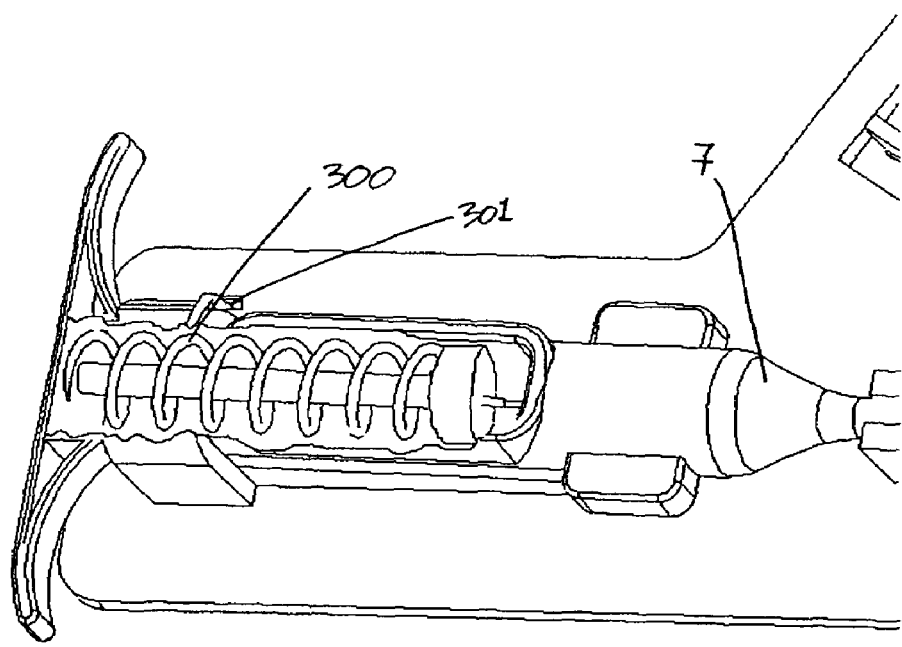
Figure 24:
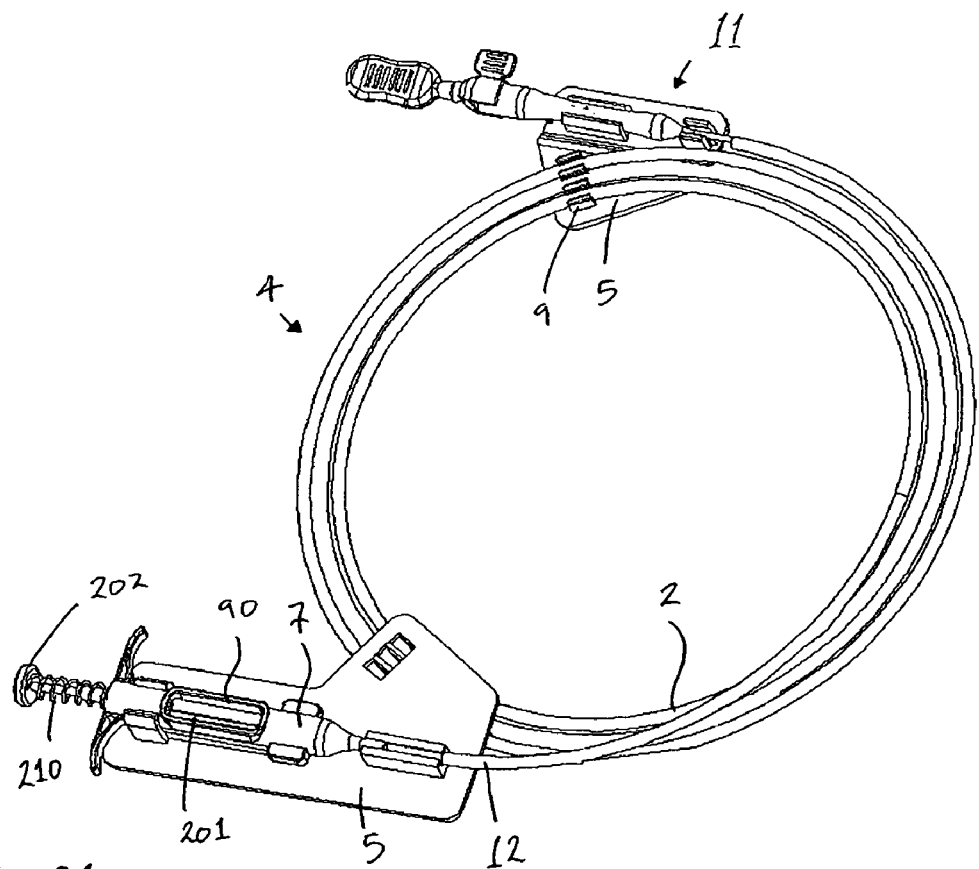
FIG. 24 is a perspective view of a pack containing an embolic protection filter, a catheter assembly, and a device according to the invention for loading the embolic protection filter into the catheter assembly.
Figure 25:
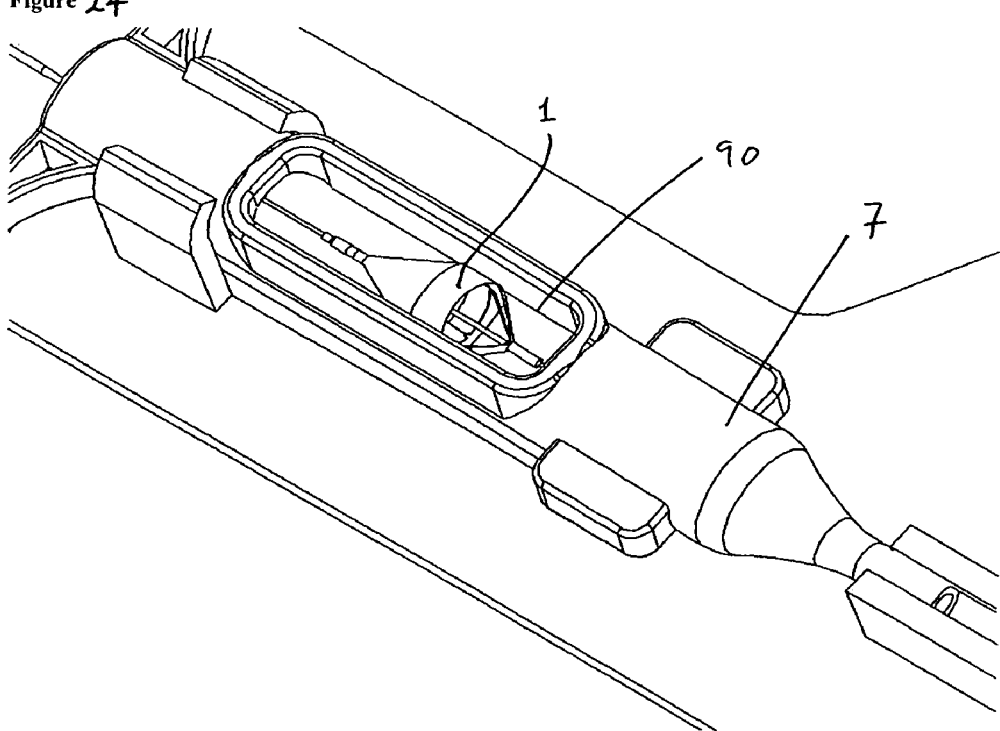
FIGS. 25 to 27 are enlarged, perspective views of a part of the pack of FIG. 24.
Figure 26:
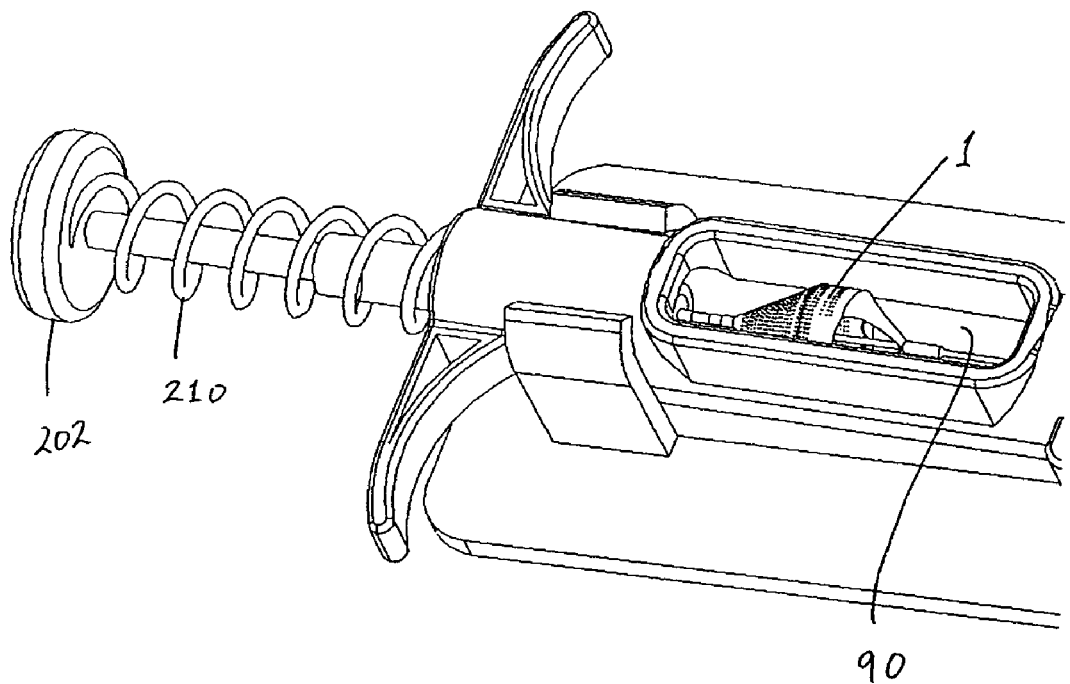

As an alternative to the moveable plunger 202 of FIGS. 18 to 23, a pre-loaded spring 300 may be used to load the filter 1 into the pod 13 of the delivery catheter 2, as illustrated in FIGS. 23(*a*) and 23(*b*). A releasable clasp 301 may be used to hold the spring 300 in a compressed state until it is desired to load the filter 1, at which time the clasp 301 may be released.

As illustrated in FIGS. 24 to 27, a coiled spring 210 may be provided extending around the plunger 202. The plunger 202 engages the filter element 1 in the bath 90, and the spring 210 engages a proximal end of the bath 90. In this manner the spring force prevents excessive loading forces being applied to the system to minimise the possibility of damage being caused during loading.

Figure 27:
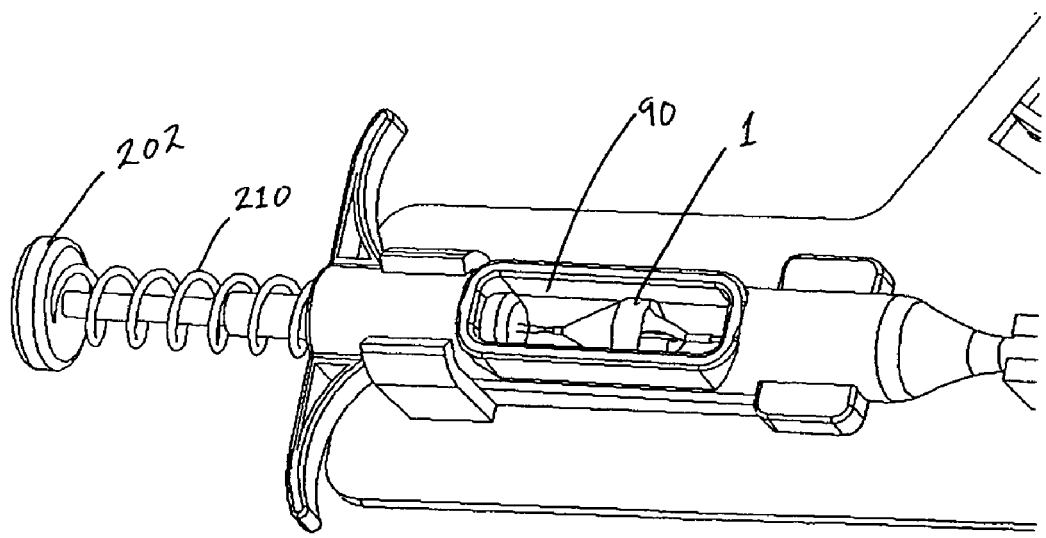
Figure 27A:
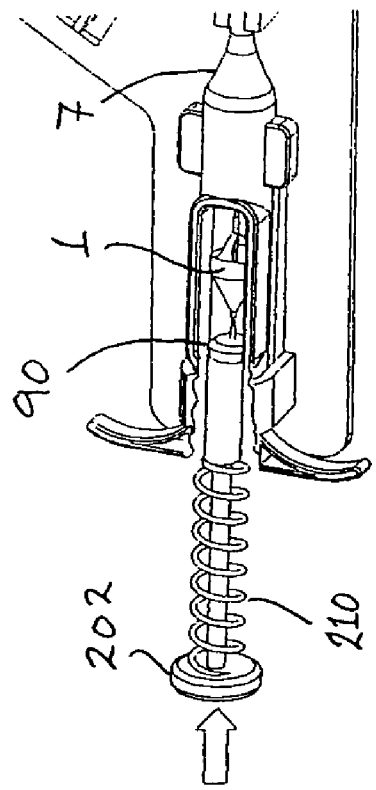
FIGS. 27(a) to 27(d) are perspective views illustrating loading of the embolic protection filter into the catheter assembly.
Figure 27B:
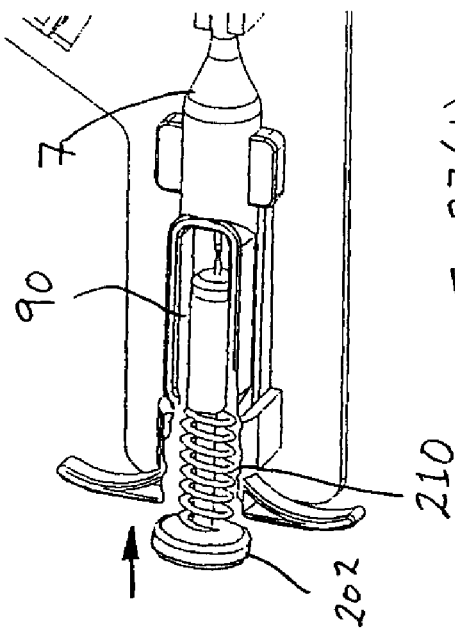
Figure 27C:
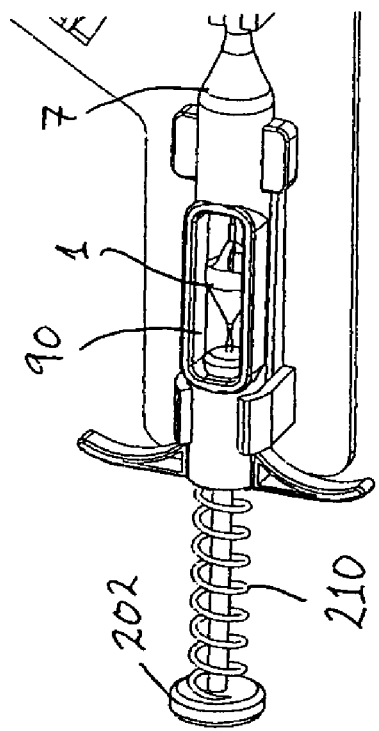
Figure 27D:
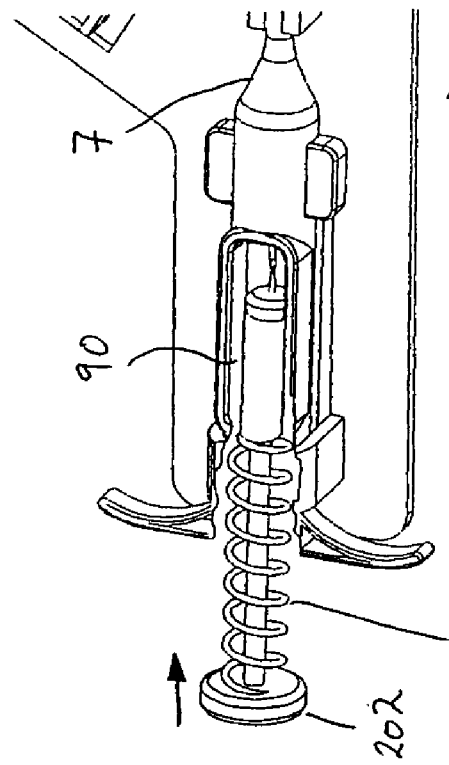
Figure 29:
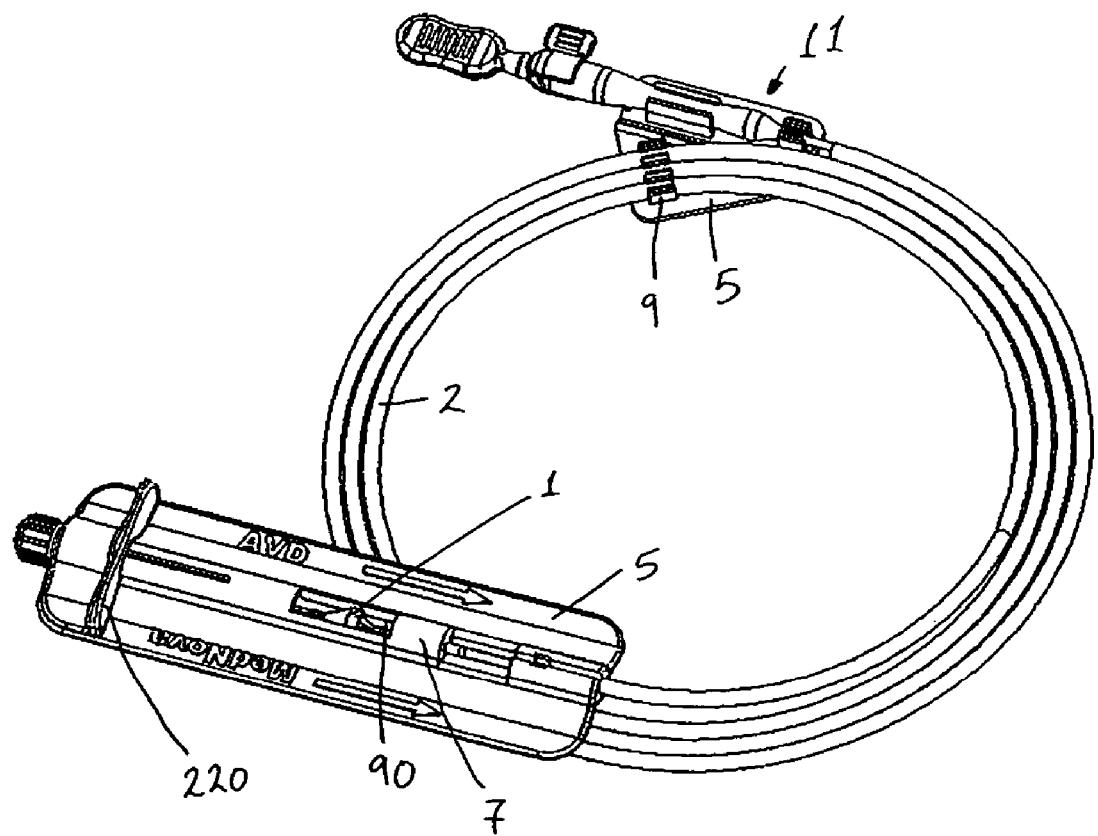
Figure 30:
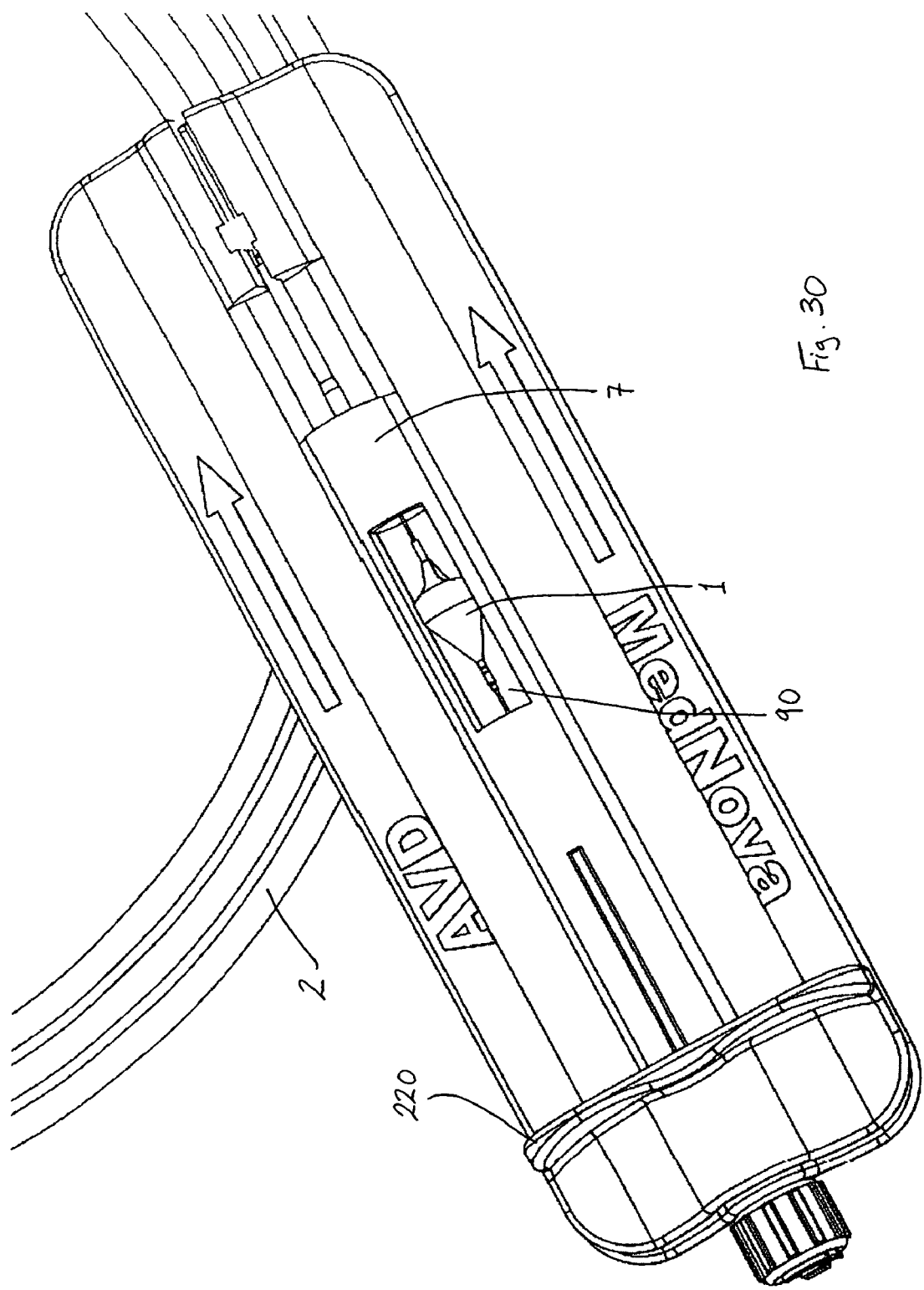
Figure 31:
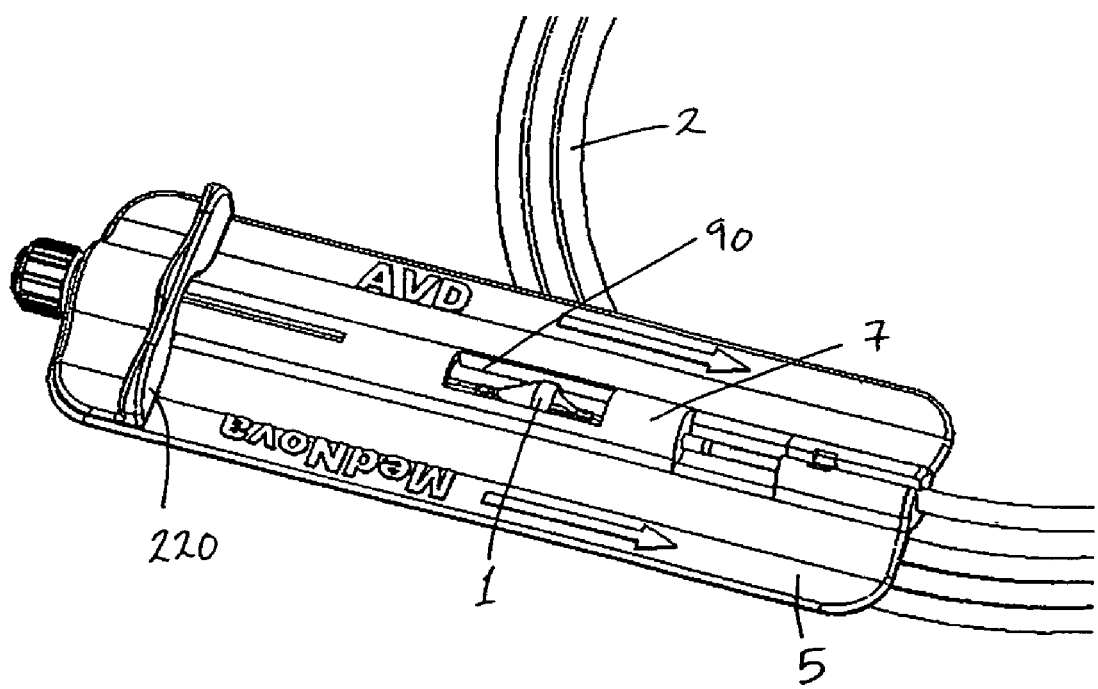
Figure 32:
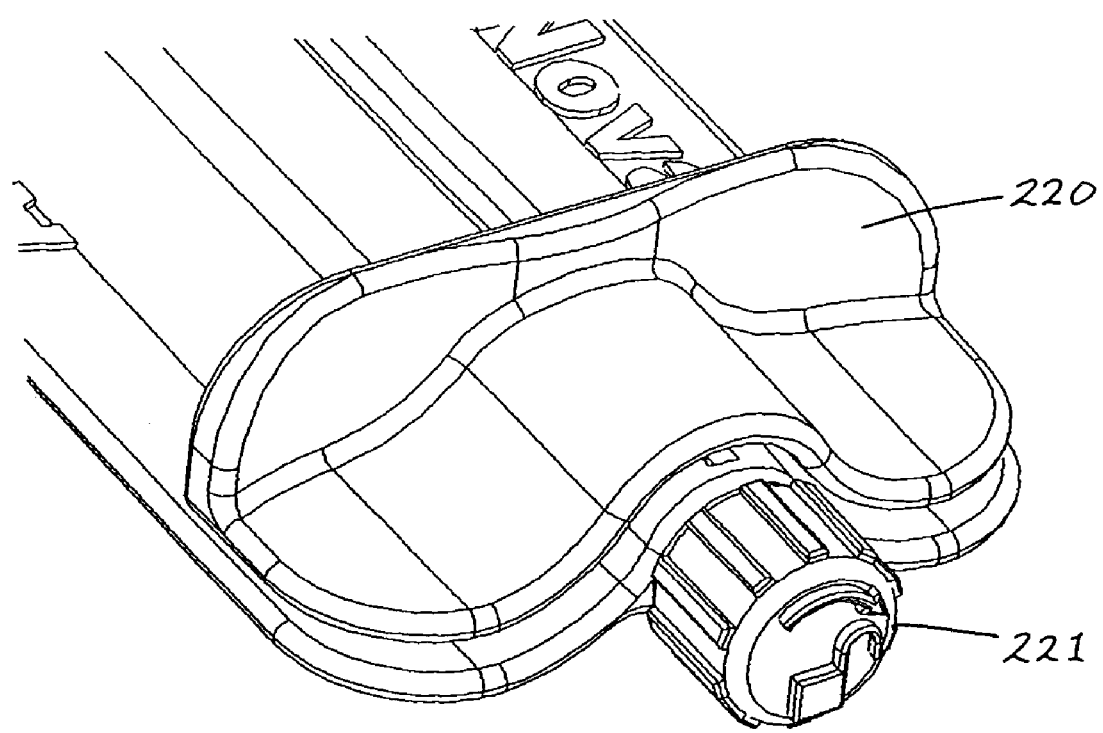
Figure 33:
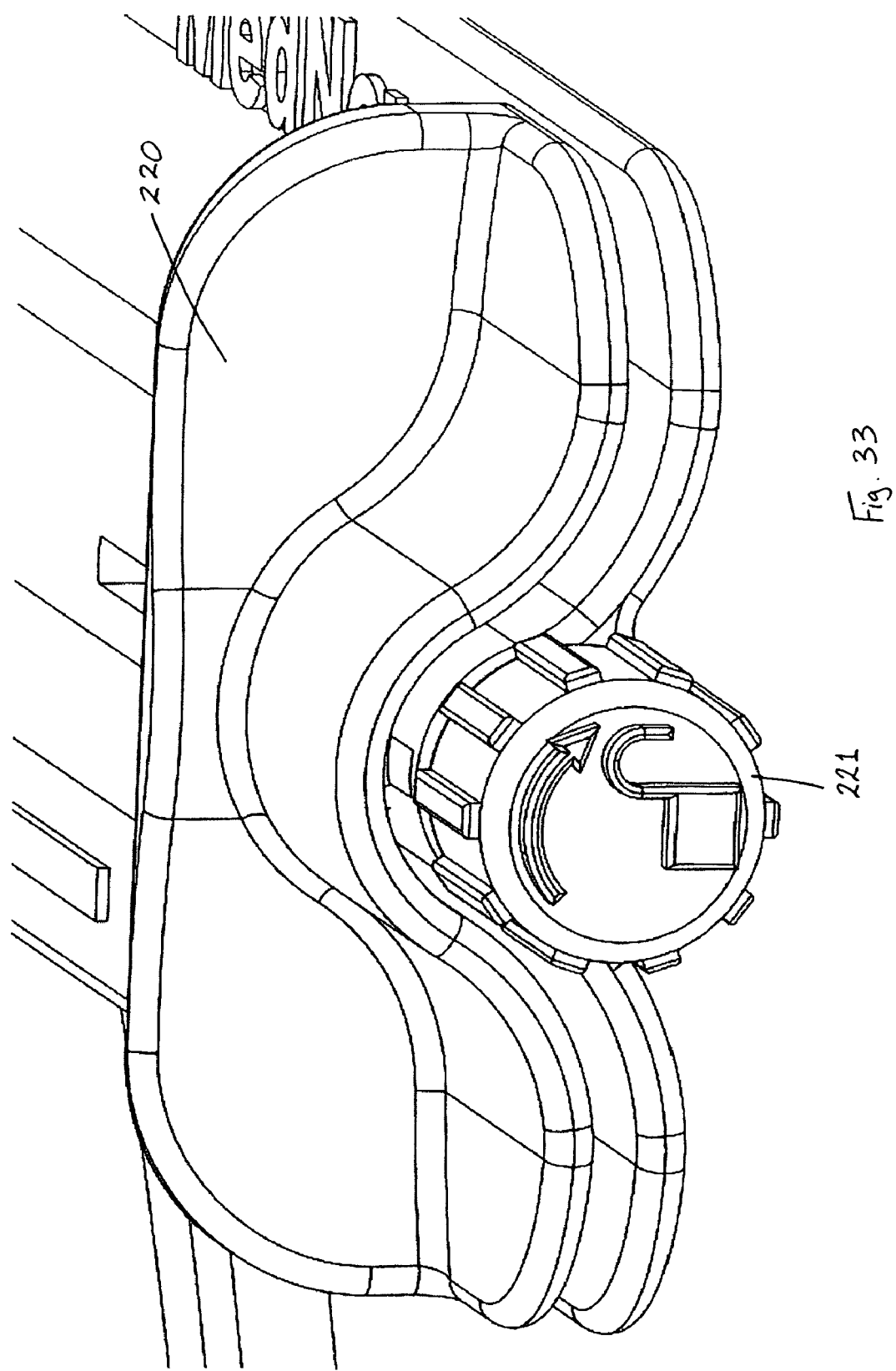
Figure 34:
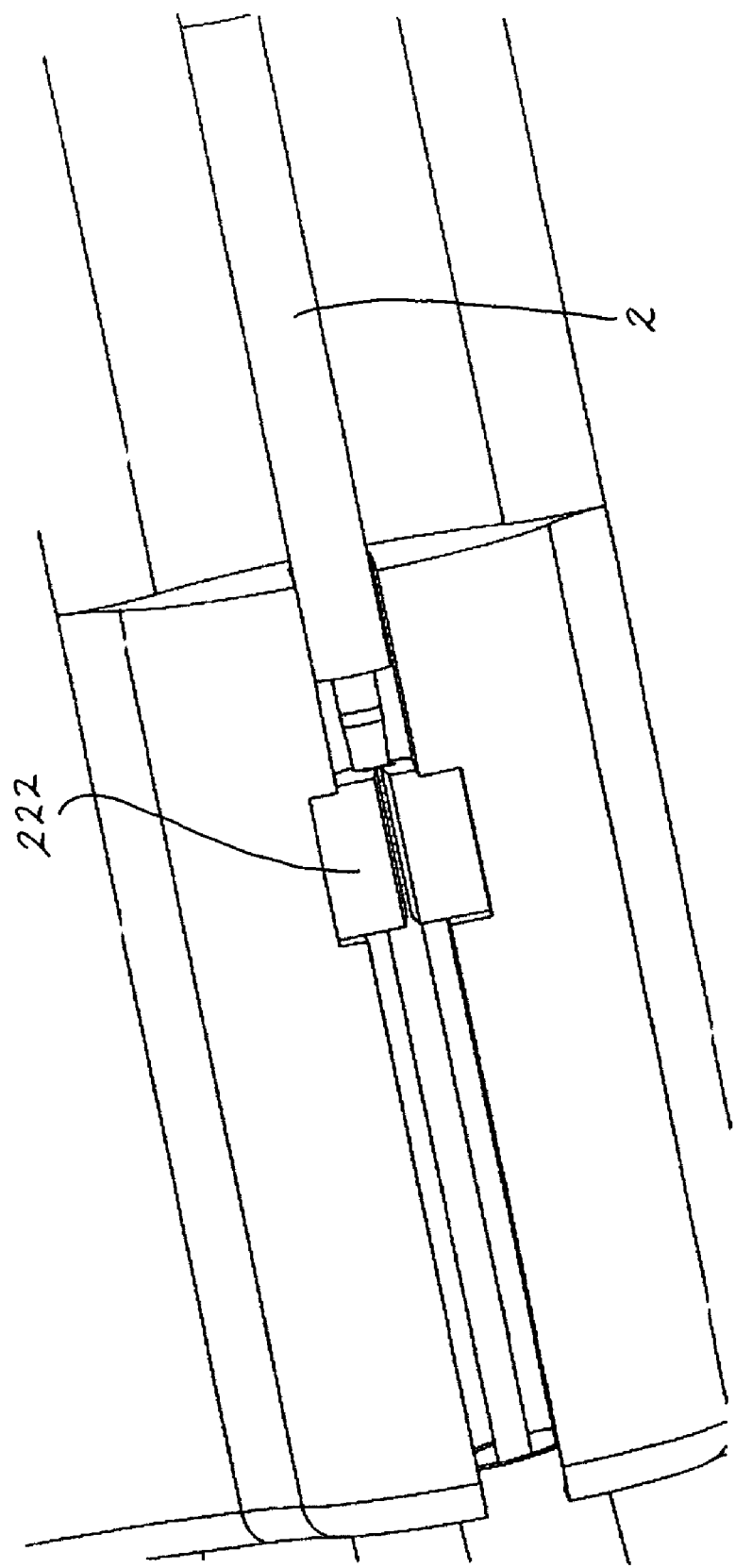
Figure 35:
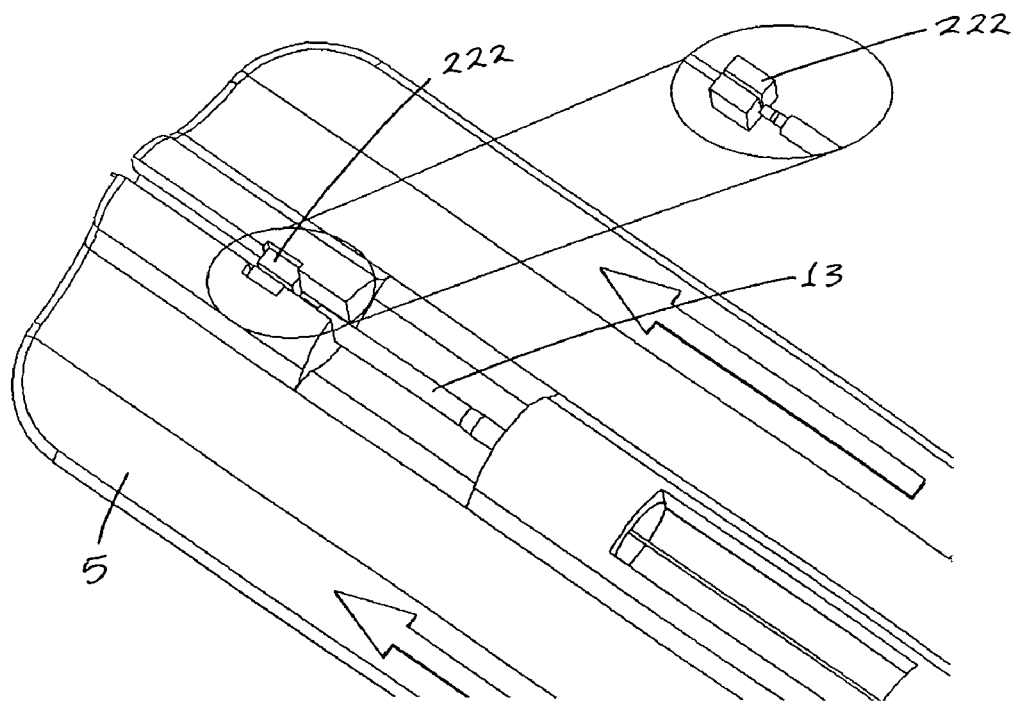
Figure 36:
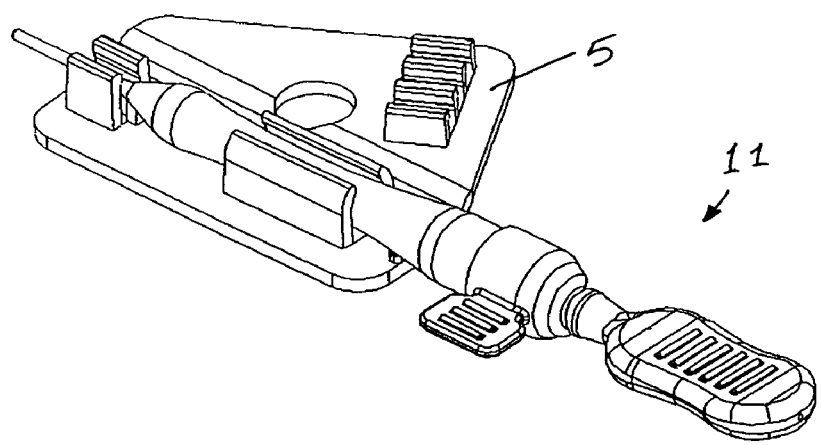

The process of loading of the filter 1 into the pod 13 of the catheter 2 is illustrated in FIGS. 27(*a*) to 27(*d*). As the plunger 202 is advanced through the bath 90, the spring 210 is compressed, thus controlling the pushing force exerted on the filter 1.

As an alternative to using a plunger, a handle mechanism 220 may be used to load the filter 1 into the pod 13, as illustrated in FIGS. 28 to 37. The handle mechanism 220 is movable relative to the pack 5 to move the filter 1 relative to the pod 13 for loading into the pod 13.

A lock mechanism 221 is provided to lock the handle 220 in position until it is desired to load the filter 1. The lock 221 may then be opened by rotating the lock mechanism.

A block 222 of elastomeric material, such as rubber is provided proximally of the pod 13. The block 222 engages against the proximal end of the pod 13 to prevent movement of the catheter 2 during loading of the filter 1. When the filter 1 is fully loaded into the pod 13, further pushing force applied at the handle mechanism 220 overcomes the elastomeric force of the block 222 to push the loaded pod 13 proximally through the block 222.

The block 222 thus acts as a means of controlling the force applied to the system during loading.

Figure 38:
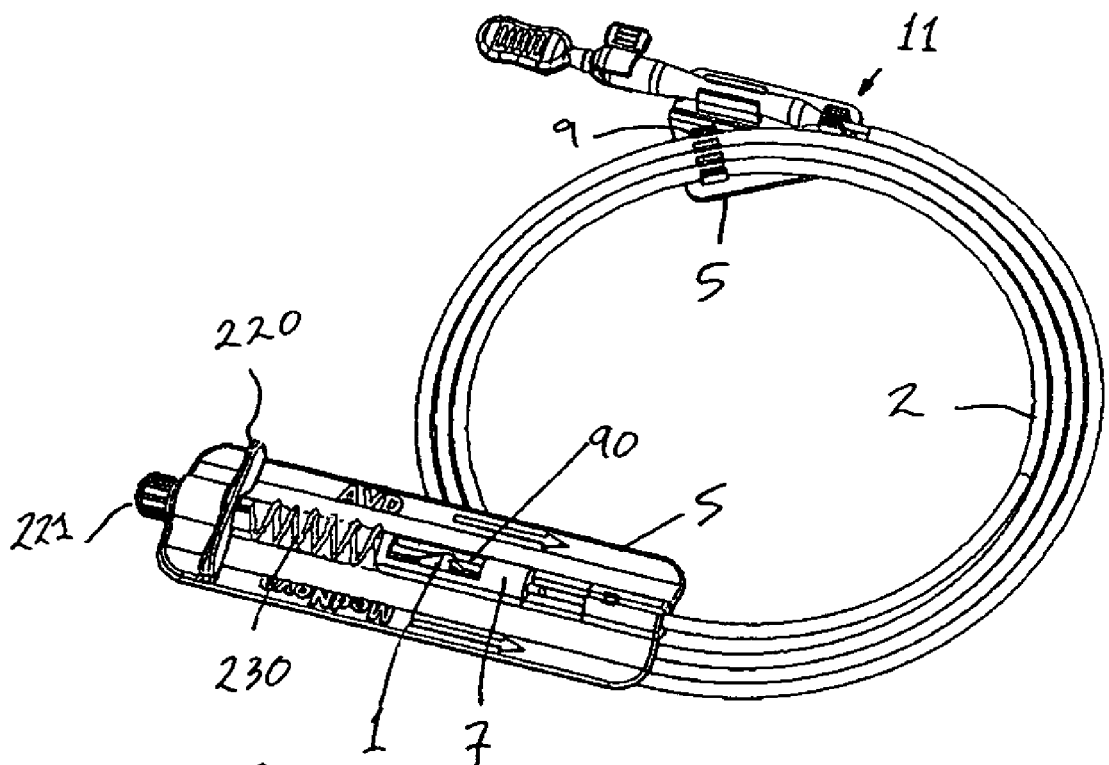
FIGS. 38 and 39 are perspective views of other packs.
Figure 39:
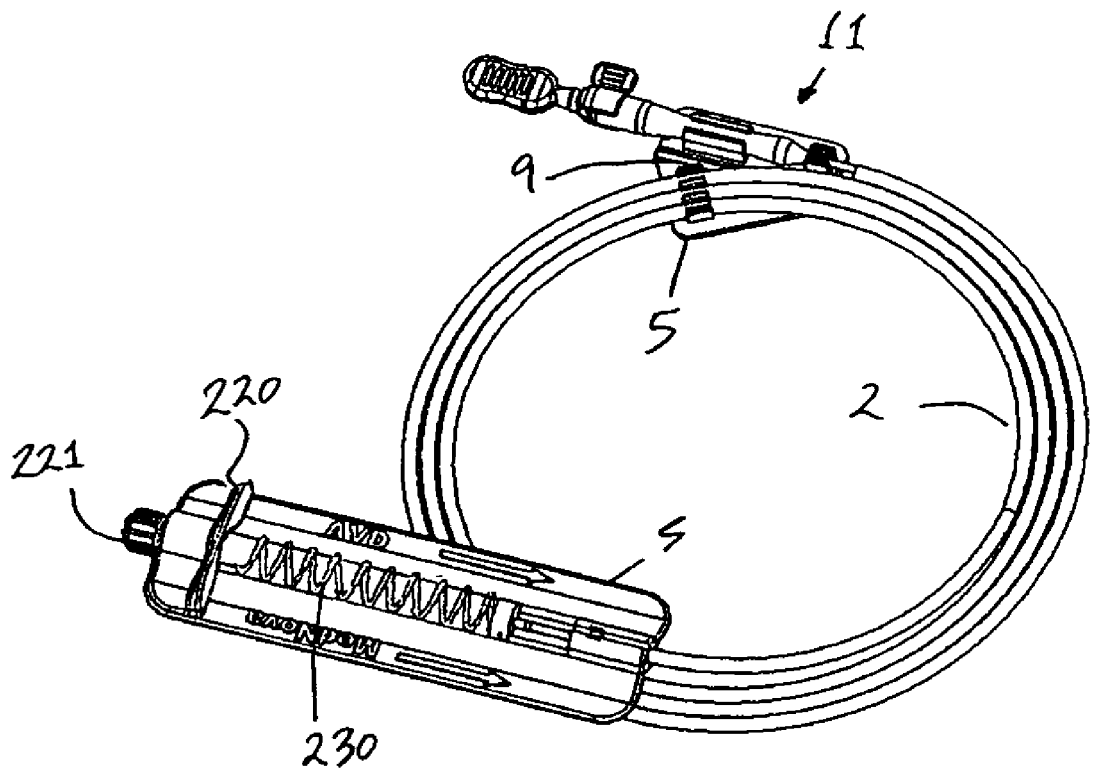
Figure 40:
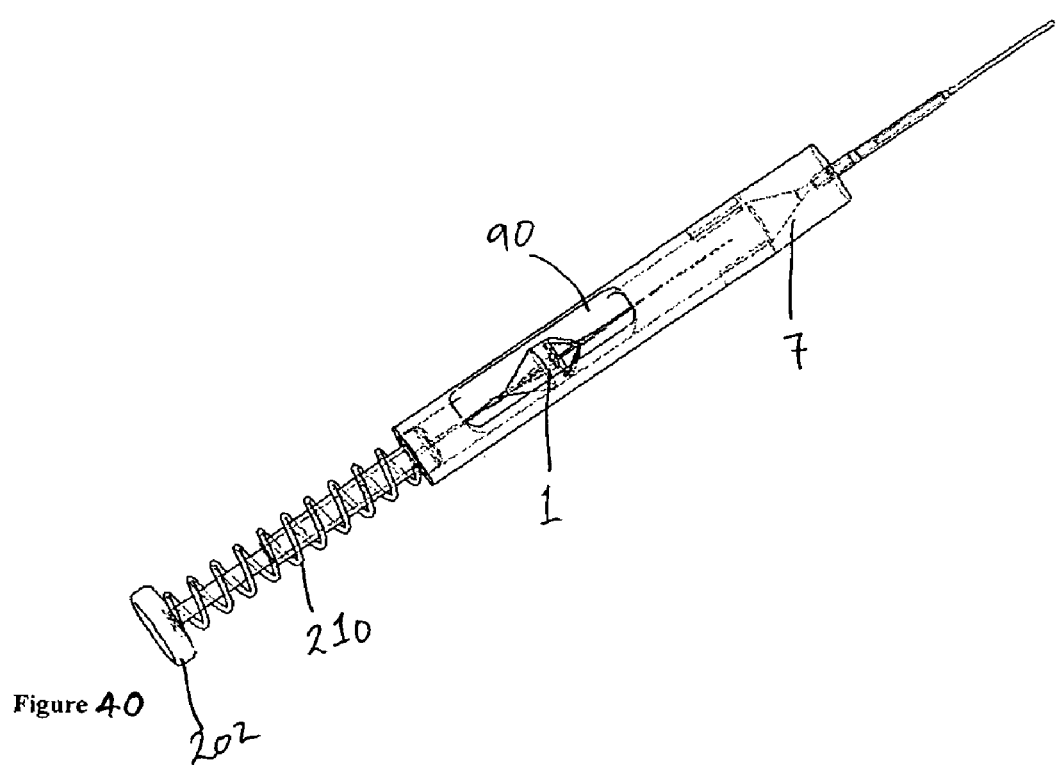
FIGS. 40 to 43 are perspective views of a further device according to the invention for loading an embolic protection filter into a catheter assembly.
Figure 41:
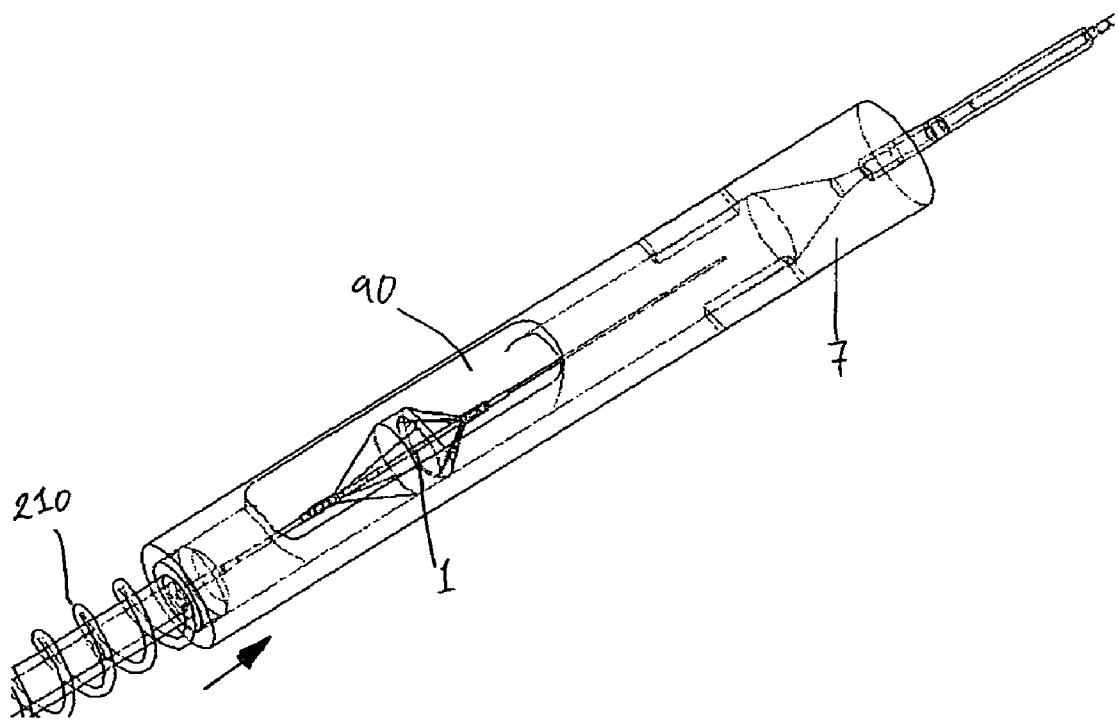
Figure 42:
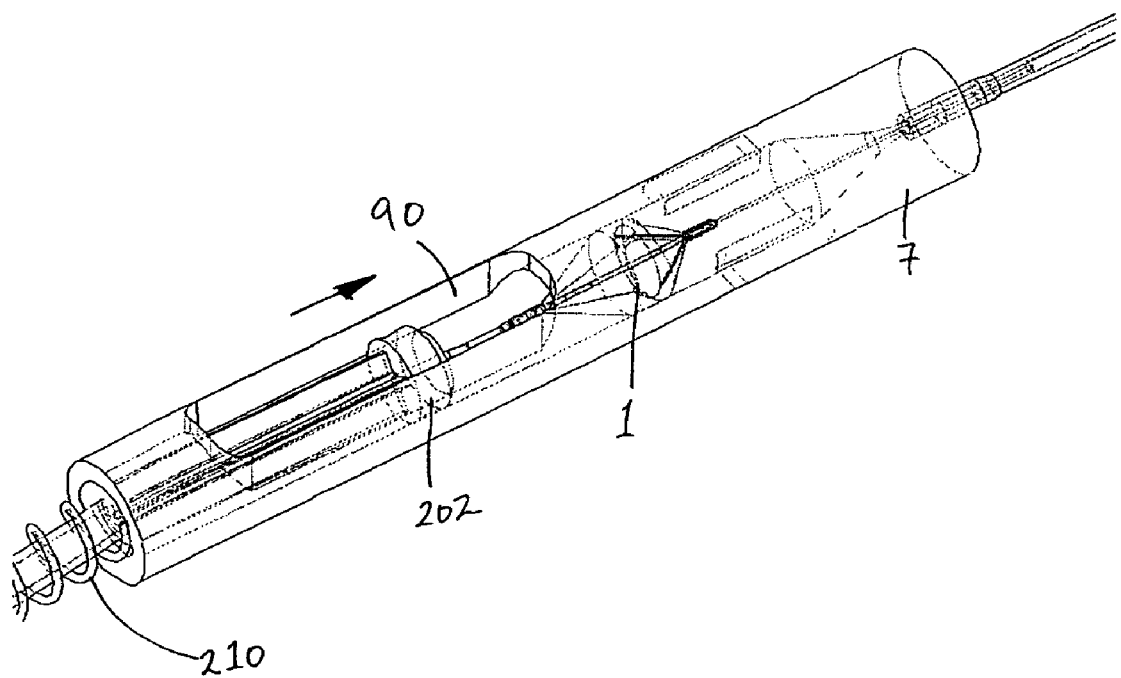
Figure 43:
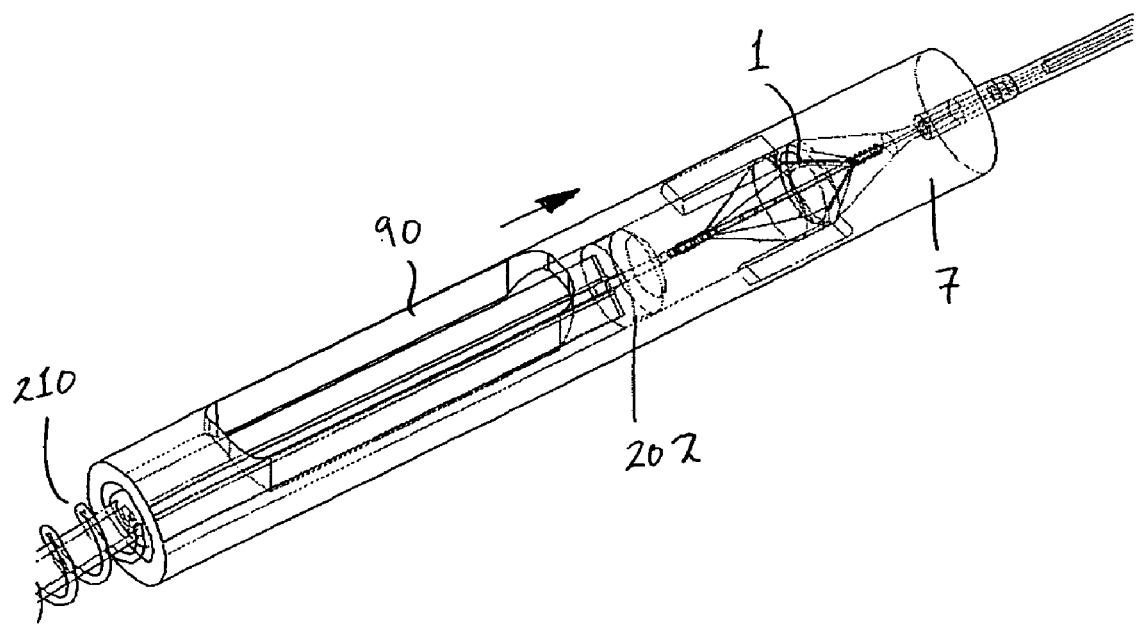
Figure 44:
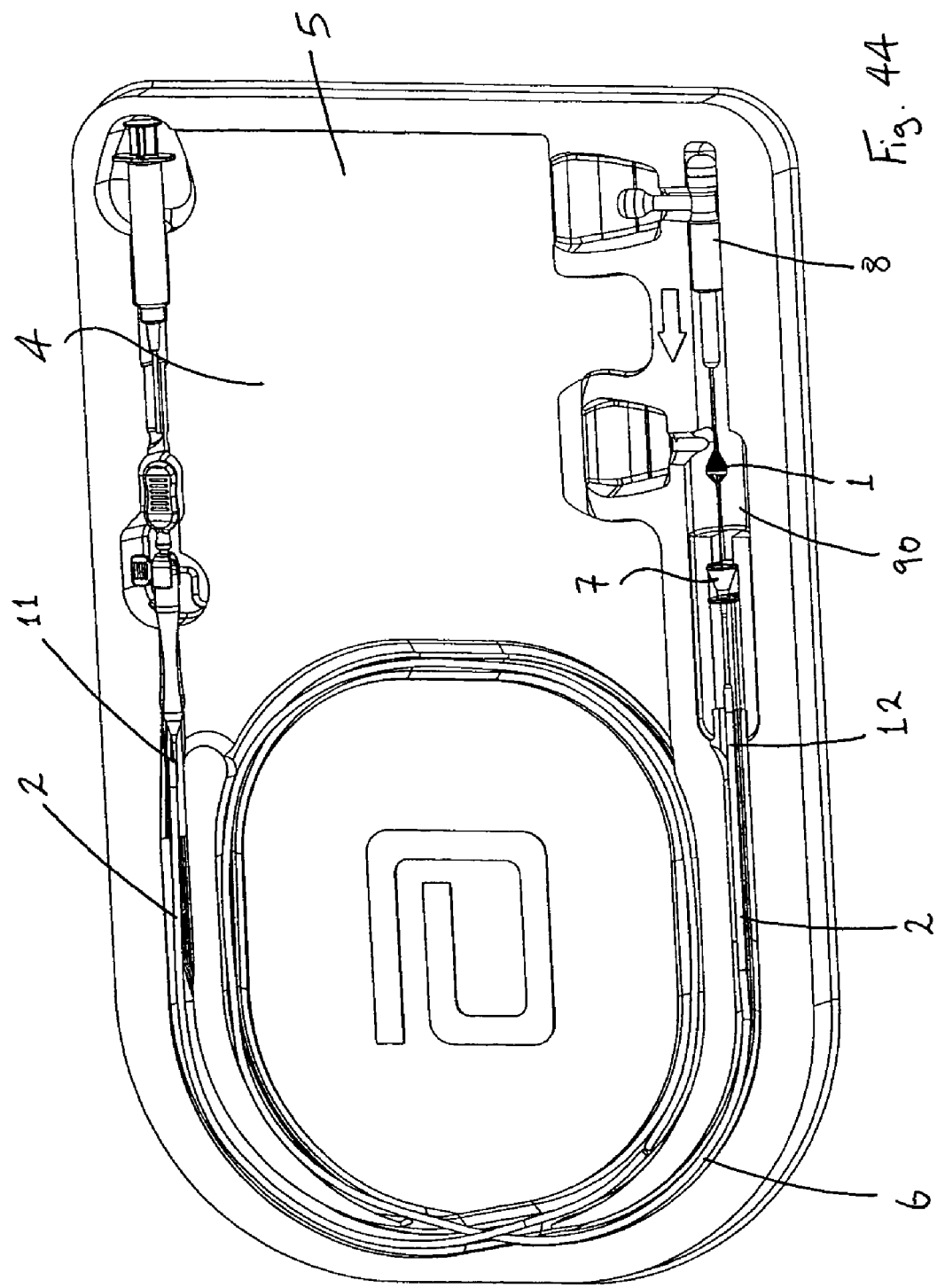
FIG. 44 is a perspective view of a pack containing an embolic protection filter, a catheter assembly, and two devices according to the invention for loading the embolic protection filter into the catheter assembly.
Figure 45:
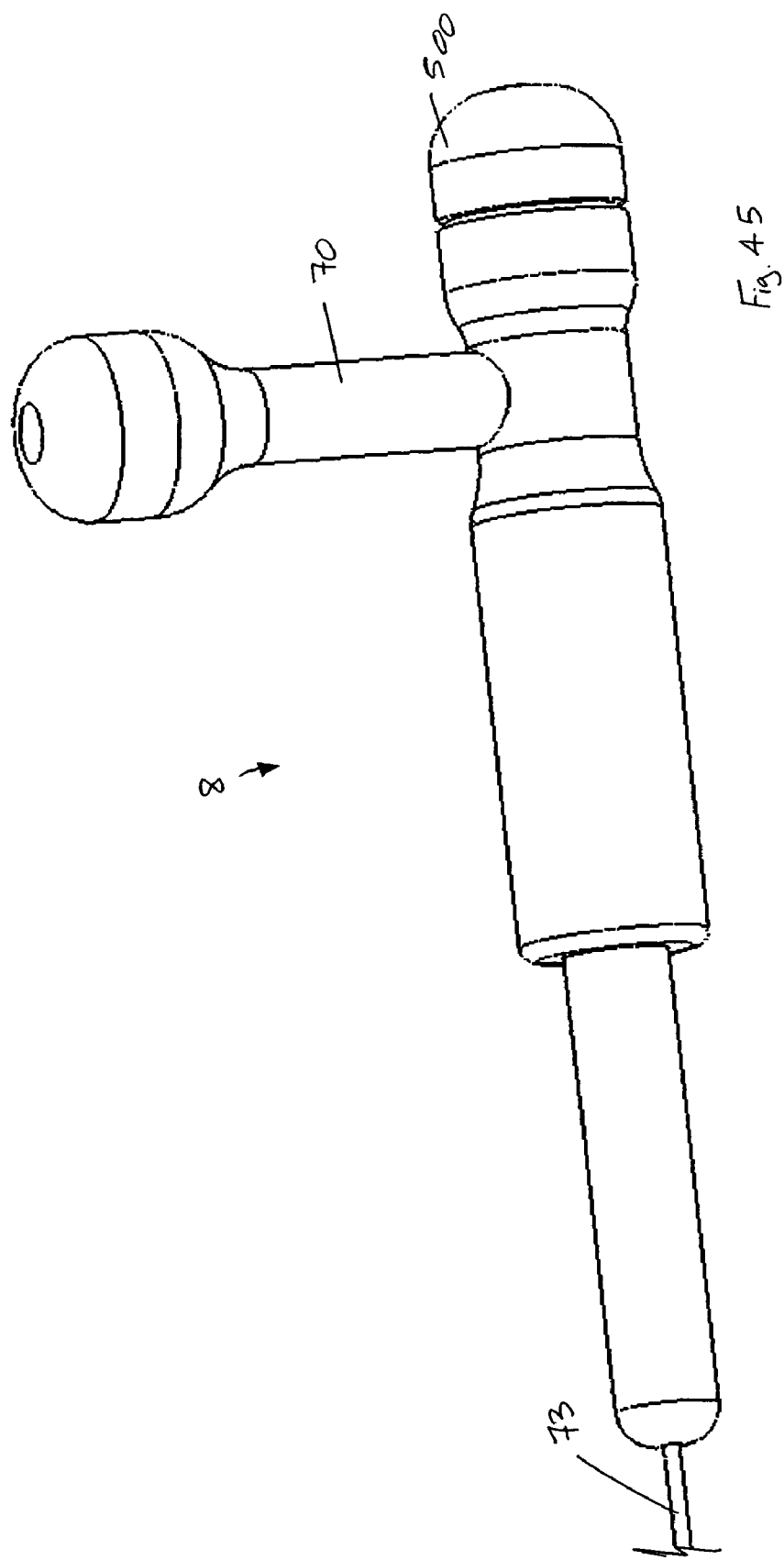
FIG. 45 is a perspective view of the first loading device of FIG. 44.

A spring 230 may be provided between the handle mechanism 220 and the filter element 1, as illustrated in FIGS. 38 and 39. The spring force prevents excessive loading force being applied to the system.

FIGS. 40 to 43 illustrate passage of the plunger 202 through the bath 90 to load the filter 1 into the pod 13 with a combined flushing of the filter 1 and/or the catheter 2.

Referring to FIGS. 44 to 50 there is illustrated another transvascular embolic protection system, which is similar to the system of FIGS. 1 to 17, and similar elements if FIGS. 44 to 50 are assigned the same reference numerals.

Figure 46:
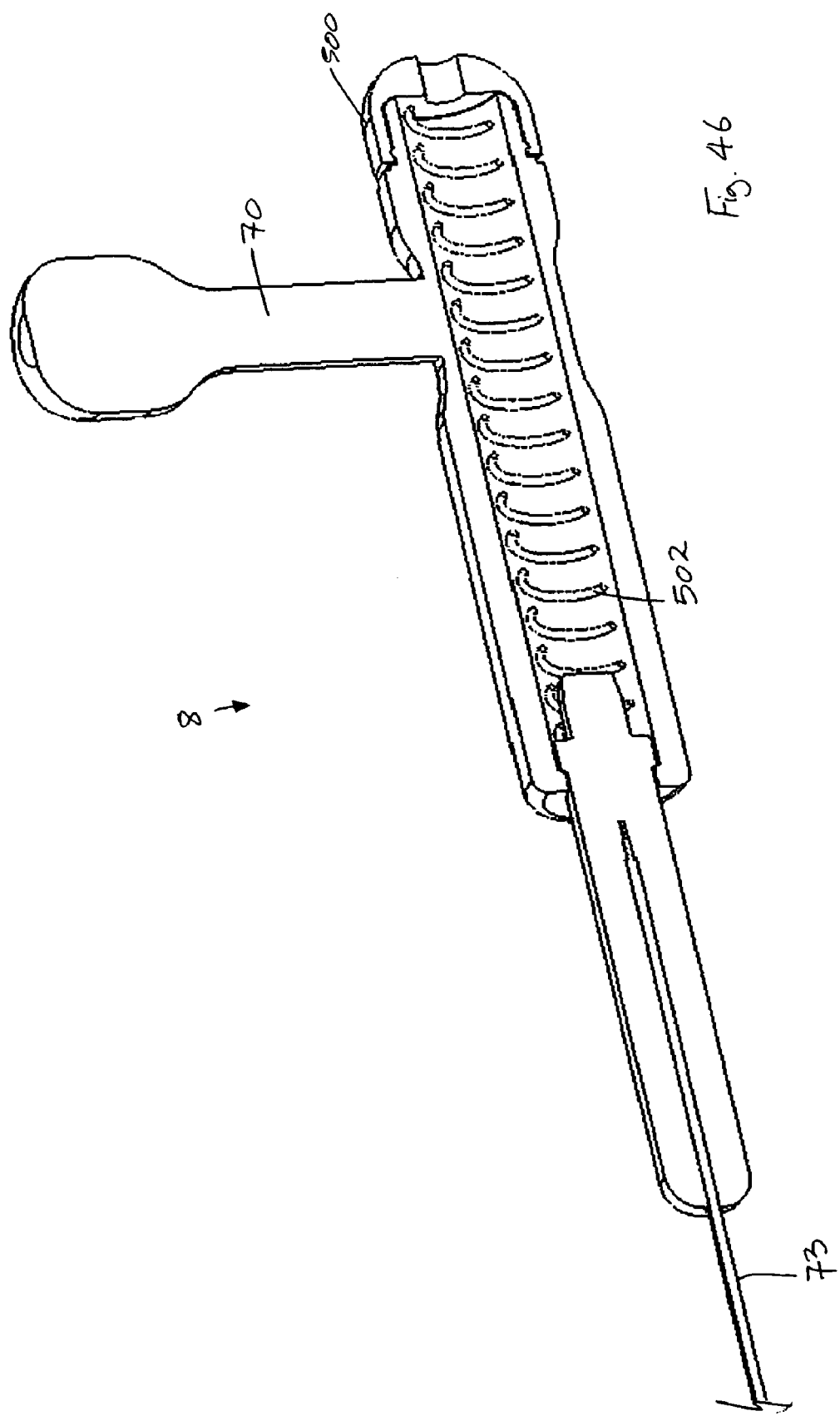
FIG. 46 is a cut-away, perspective view of the loading device of FIG. 45.

An end cap 500 is releasably attached to the pushing device 8 in a snap-fit manner to aid assembly (FIG. 46). It will be appreciated that the end cap 500 may be attached to the pushing device 8 in a variety of possible means, for example by means of a screw-thread or by means of an adhesive.

Figure 47:
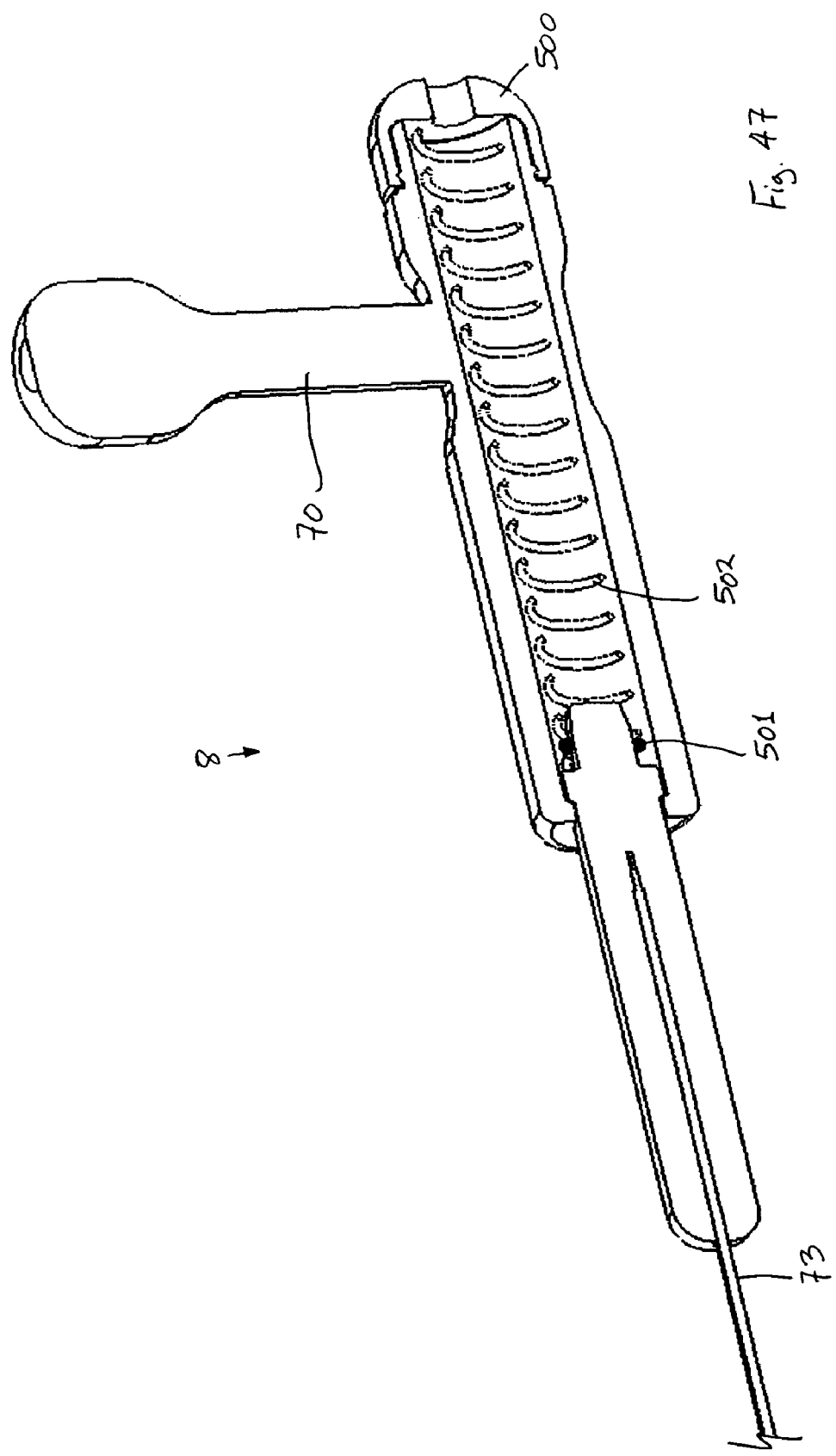
FIG. 47. is a view similar to FIG. 46 of another loading device according to the invention.
Figure 48:
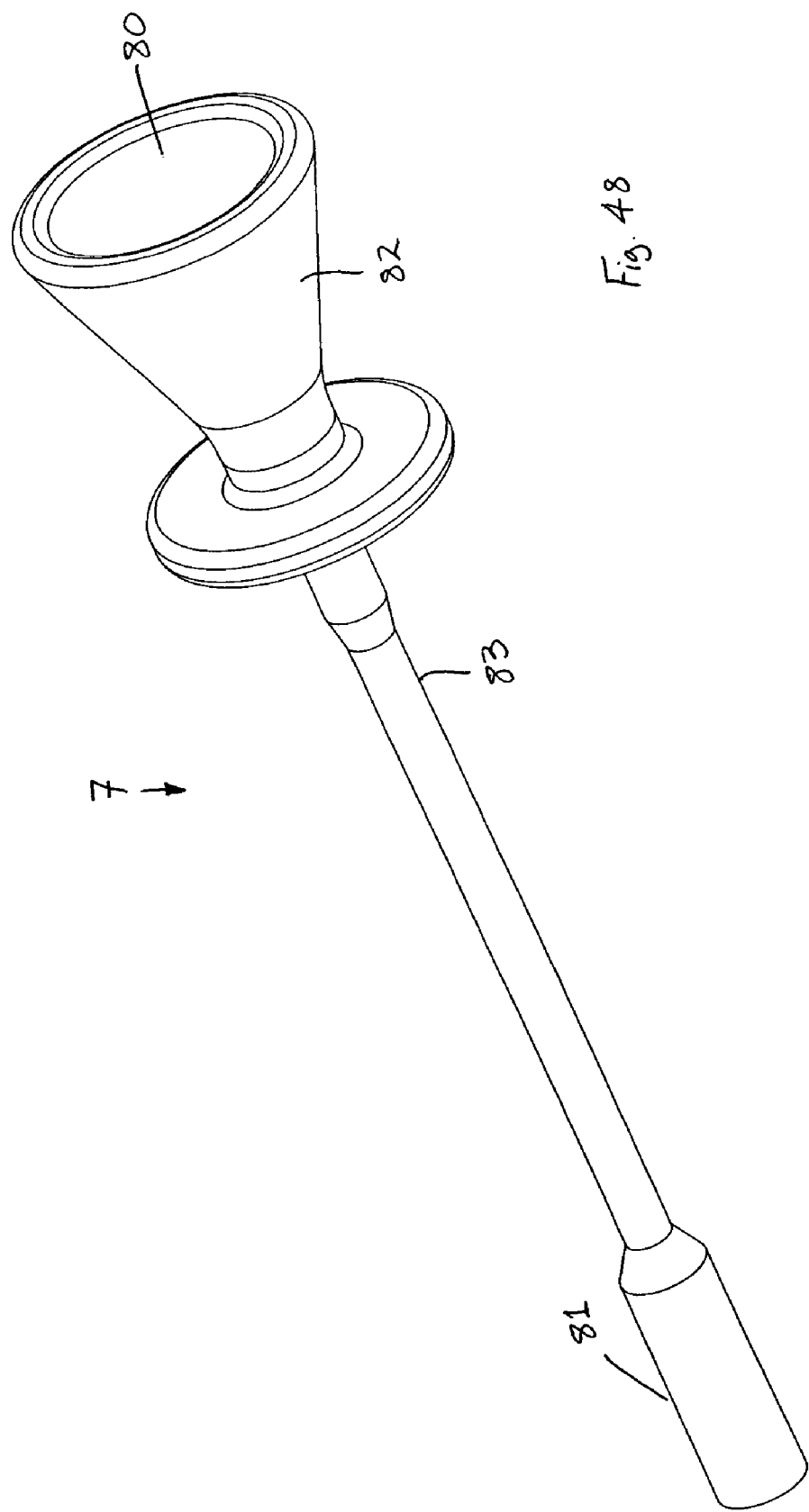
FIG. 48 is a perspective view of the second loading device of FIG. 44.

A ridge 501 may be provided to assist in keeping the spring 502 in the desired position relative to the handle 70 (FIG. 47).

Figure 49:
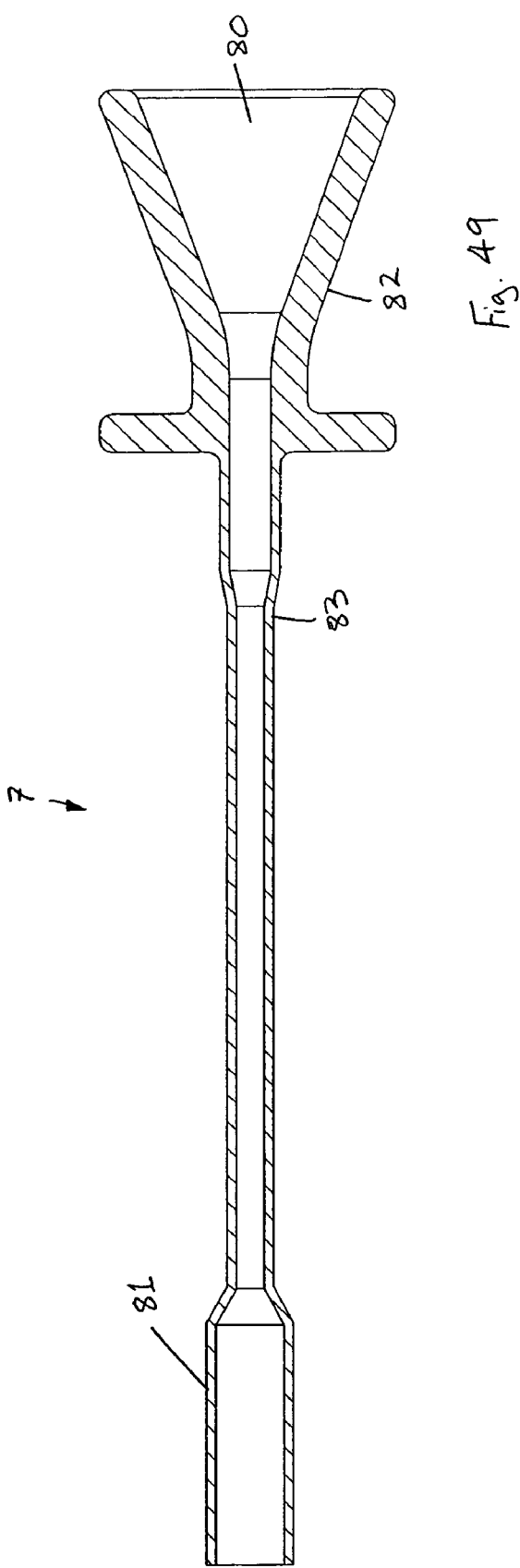
FIG. 49 is a cross-sectional, side view of the loading device of FIG. 48.
Figure 50:
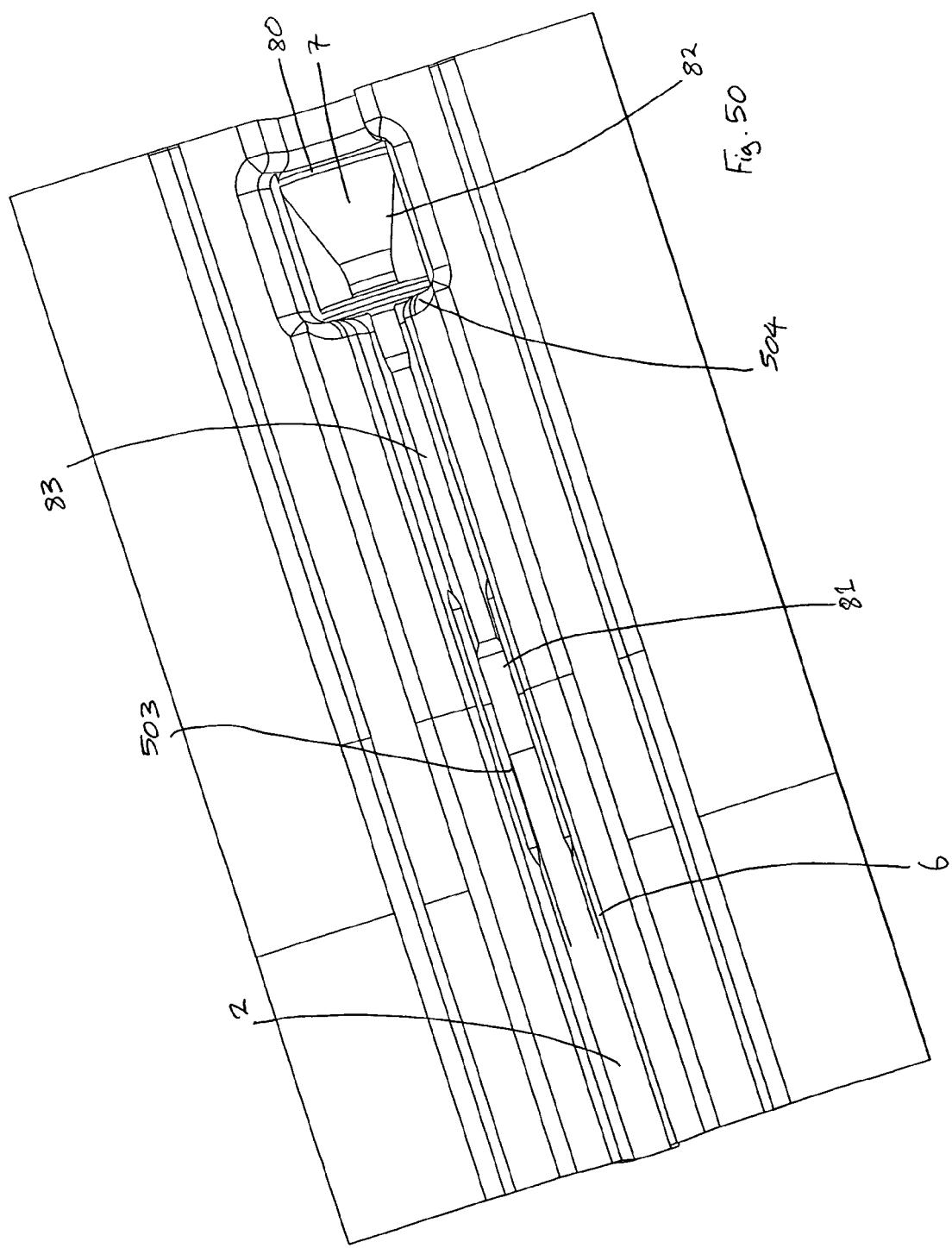
FIG. 50 is a perspective view of the loading device of FIG. 48 mounted in the tray of FIG. 44.

In this case the loading device 7 is provided in the form of a one-piece loading funnel (FIG. 49). As illustrated in FIG. 50, a snap-fit projection 503 on the channel 6 holds the proximal end of the loading device 7 in position. A corner edge 504 at the end of the channel 6 provides an abutment during loading of the filter 1.

The invention is not limited to the embodiments hereinbefore described, with reference to the accompanying drawings, which may be varied in construction and detail.

The invention claimed is:

1. A device for loading an embolic protection filter into a catheter, the device comprising:
   an engagement member for engaging an embolic protection filter, the engagement member configured to load the embolic protection filter into a catheter; and
   a controller to control a loading force exerted on the embolic protection filter by the engagement member during loading into the catheter,
   wherein the controller is provided by a first part of the device being movable relative to a second part of the device.

2. A device as claimed in claim 1 wherein the first part of the device is movable relative to the second part of the device between an extended configuration and a retracted configuration.

3. A device as claimed in claim 2 wherein the device is biased towards the extended configuration.

4. A device as claimed in claim 3 wherein the device comprises a biasing member to bias the device towards the extended configuration.

5. A device as claimed in claim 4 wherein the biasing member comprises a coiled spring.

6. A device as claimed in claim 1 wherein the first part of the device comprises a handle part.

7. A device as claimed in claim 1 wherein the second part of the device comprises the engagement member.

8. A device as claimed in claim 1 wherein the engagement member comprises a pusher for engaging an embolic protection filter to push the embolic protection filter into a catheter.

9. A device as claimed in claim 1 wherein the engagement member comprises a puller for engaging an embolic protection filter to pull the embolic protection filter into a catheter.

10. A device as claimed in claim 1 wherein the engagement member is provided on an elongate stem.

11. A device as claimed in claim 10 wherein the engagement member is integral with the stem.

12. A device as claimed in claim 11 wherein the engagement member comprises a step in the stem from a small diameter portion to a large diameter portion.

13. A device as claimed in claim 10 wherein the stem comprises a wire.

* * * * *